(12) United States Patent
Pompilio et al.

(10) Patent No.: US 12,006,514 B2
(45) Date of Patent: Jun. 11, 2024

(54) METHOD FOR THE ISOLATION OF SUBPOPULATIONS OF CARDIAC PROGENITOR CELLS AND RELATED USES IN THE MEDICAL FIELD

(71) Applicants: CENTRO CARDIOLOGICO MONZINO SPA, Milan (IT); UNIVERSITA' DEGLI STUDI DI MILANO, Milan (IT)

(72) Inventors: Giulio Pompilio, Milan (IT); Elisa Gambini, Sovico (IT); Gabriella Spaltro, Truccazzano (IT)

(73) Assignee: OLOKER THERAPEUTICS S.R.L., Bari (IT)

( * ) Notice: Subject to any disclaimer, the term of this patent is extended or adjusted under 35 U.S.C. 154(b) by 769 days.

(21) Appl. No.: 16/617,429

(22) PCT Filed: Jun. 6, 2018

(86) PCT No.: PCT/IB2018/054057
§ 371 (c)(1),
(2) Date: Nov. 26, 2019

(87) PCT Pub. No.: WO2018/224983
PCT Pub. Date: Dec. 13, 2018

(65) Prior Publication Data
US 2020/0140818 A1  May 7, 2020

(30) Foreign Application Priority Data
Jun. 7, 2017 (IT) .................. 102017000062176

(51) Int. Cl.
| | | |
|---|---|---|
| *C12N 5/077* | (2010.01) | |
| *A61K 35/34* | (2015.01) | |
| *G01N 1/28* | (2006.01) | |
| *G01N 33/569* | (2006.01) | |

(52) U.S. Cl.
CPC ............ *C12N 5/0657* (2013.01); *A61K 35/34* (2013.01); *G01N 1/286* (2013.01); *G01N 33/56966* (2013.01); *C12N 2500/30* (2013.01); *C12N 2501/115* (2013.01); *C12N 2501/14* (2013.01); *G01N 2001/2873* (2013.01)

(58) Field of Classification Search
CPC ........................... C12N 5/0657; C12N 5/0667
See application file for complete search history.

(56) References Cited

U.S. PATENT DOCUMENTS

| | | | | |
|---|---|---|---|---|
| 2008/0075750 | A1* | 3/2008 | Akins, Jr. ......... | A61K 38/1866 435/41 |
| 2015/0216905 | A1* | 8/2015 | Kreke ................ | A61K 35/34 435/381 |
| 2015/0273113 | A1 | 10/2015 | Marban et al. | |

FOREIGN PATENT DOCUMENTS

| | | |
|---|---|---|
| JP | 2016-516423 A | 6/2016 |
| WO | 2011057249 A2 | 5/2011 |

OTHER PUBLICATIONS

Sigma Cell Culture Manual 2011-2014 (Year: 2011).*
Matsuda et al.. Human cardiac stem cells with reduced notch signaling show enhanced therapeutic potential in a rat acute infarction model. Circ J. 2014;78(1):222-31. doi: 10.1253/circj.cj-13-0534. Epub Oct. 9, 2013. PMID: 24107361. (Year: 2013).*
Serva Electrophoresis Catalog 2014 (Year: 2014).*
Sharma S, et al. Cardiosphere-derived cells from pediatric end-stage heart failure patients have enhanced functional activity due to the heat shock response regulating the secretome. Stem Cells. Apr. 2015;33(4):1213-29. doi: 10.1002/stem.1937. PMID: 25752510; PMCID: PMC4801025. (Year: 2015).*
Hodonsky et al. Effects of scaffold material used in cardiovascular surgery on mesenchymal stem cells and cardiac progenitor cells. Annals of Thoracic Surgery 2015, 99:605-611. (Year: 2015).*
Itzhaki-Alfia et al. Patient characteristics and cell source determine the No. of isolated human cardiac progenitor cells. Circulation 2009, 120:2559-2566. (Year: 2009).*
Vella et al. PIWI-interacting RNA (piRNA) signatures in human cardiac progenitor cells. International Journal of Biochemistry & Cell Biology 2016, 76:1-11. (Year: 2016).*
Anke M Smits et al: "Human cardiomyocyte progenitor cells differentiate into functional mature cardiomyocytes: an in vitro model for studying human cardiac physiology and pathophysiology", Nature Protocols, vol. 4, No. 2, Feb. 1, 2009 (Feb. 1, 2009), GB, pp. 232-243, XP055504021, ISSN: 1754-2189, DOI: 10.1038/nprot.2008.229.
Deliang Shen et al: "Therapeutic benefits of CD90-negative cardiac stromal cells in rats with a 30-day chronic infarct", Journal of Cellular and Molecular Medicine, vol. 22, No. 3, Jan. 17, 2018 (Jan. 17, 2018), RO, pp. 1984-1991, XP055503995, ISSN: 1582-1838, DOI: 10.1111/jcmm.13517.
Dergilev K V et al: "Isolation and characterization of cardiac progenitor cells from myocardial right atrial appendage tissue", Cell and Tissue Biology, Springer US, Boston, vol. 10, No. 5, Oct. 20, 2016 (Oct. 20, 2016), pp. 349-356, XP036079464, ISSN: 1990-519X, [retrieved on Oct. 20, 2016], DOI: 10.1134/S1990519X16050035.
Elisa Gambini et al: "C-kit+ cardiac progenitors exhibit mesenchymal markers and preferential cardiovascular commitment", Cardiovascular Research, vol. 89, No. 2, Sep. 10, 2010 (Sep. 10, 2010), GB, pp. 362-373, XP055422739, ISSN: 0008-6363, DOI: 10.1093/cvr/cvq292.

(Continued)

*Primary Examiner* — Allison M Fox
*Assistant Examiner* — Jennifer S Spence
(74) *Attorney, Agent, or Firm* — Florek & Endres PLLC

(57) ABSTRACT

The present invention relates to a method for the isolation of subpopulations of cardiac progenitor cells from a heart tissue sample, the population thus obtained and the related uses in the medical field for the cell therapy or cardiac cell and/or tissue transplantation field.

17 Claims, 16 Drawing Sheets

(56) References Cited

OTHER PUBLICATIONS

Elisa Gambini et al: "Supplementary Material Online to C-kit+ cardiac progenitors exhibit mesenchymal markers and preferential cardiovascular commitment", Cardiovascular Research 89(2):362-373, Feb. 1, 2011 (Feb. 1, 2011), XP055422751, Retrieved from the Internet <URL:https://academic.oup.com/cardiovascres/article-lookup/doi/10.1093/cvr/cvq292#85243239> [retrieved on Nov. 8, 2017].

Elisa Gambini et al: "Patient profile modulates cardiac c-kit+ progenitor cell availability and amplification potential", Translational Research, vol. 160, No. 5, Nov. 1, 2012 (Nov. 1, 2012), NL, pp. 363-373, XP055422734, ISSN: 1931-5244, DOI: 10.1016/j.trsl.2012.05.009.

K. Cheng et al: "Relative Roles of CD90 and c-Kit to the Regenerative Efficacy of Cardiosphere-Derived Cells in Humans and in a Mouse Model of Myocardial Infarction", Journal of the American Heart Association, vol. 3, No. 5, Oct. 9, 2014 (Oct. 9, 2014), pp. e001260-e001260, XP055271592, ISSN: 2047-9980, DOI: 10.1161/JAHA.114.001260.

Megan M. Monsanto et al: "Concurrent Isolation of 3 Distinct Cardiac Stem Cell Populations From a Single Human Heart BiopsyNovelty and Significance", Circulation Research., vol. 121, No. 2, Apr. 26, 2017 (Apr. 26, 2017), US, pp. 113-124, XP055503989, ISSN: 0009-7330, DOI: 10.1161/CIRCRESAHA.116.310494.

Nuria Gago-Lopez et al: "THY-1 Receptor Expression Differentiates Cardiosphere-Derived Cells with Divergent Cardiogenic Differentiation Potential", Stem Cell Reports, vol. 2, No. 5, May 1, 2014 (May 1, 2014), United States, pp. 576-591, XP055515311, ISSN: 2213-6711, DOI: 10.1016/j.stemcr.2014.03.003.

R. Bolli et al: "Cardiac stem cells in patients with ischaemic cardiomyopathy (SCIPIO): initial results of a randomised phase 1 trial", LANCET, vol. 378, No. 9806, Nov. 14, 2011 (Nov. 14, 2011), pp. 1847-1857, XP055146402, DOI: 10.1016/S0140-6736(11)61590-0.

Spandan Kalra et al: "Can Human Pluripotent Stem Cell-Derived Cardiomyocytes Advance Understanding of Muscular Dystrophies?", Journal of Neuromuscular Diseases Sep. 22, 2015, vol. 3, No. 3, Aug. 30, 2016 (Aug. 30, 2016), pp. 309-332, XP055431805, ISSN: 2214-3599, DOI: 10.3233/JND-150133.

Stephan Detert et al: "The atrial appendage as a suitable source to generate cardiac-derived adherent proliferating cells for regenerative cell-based therapies", Journal of Tissue Engineering and Regenerative Medicine, vol. 12, No. 3, Nov. 21, 2017 (Nov. 21, 2017), US, pp. e1404-e1417, XP055515165, ISSN: 1932-6254, DOI: 10.1002/term.2528.

Brenz Verca, Stefano, "International Search Report and Written Opinion of the International searching Authority for PCT Application No. PCT/IB2018/054057," European Patent Office, Oct. 22, 2018.

Pfitzner, Gabrielle, "Notification of Transmittal of the International Preliminary Report on Patentability," International Preliminary Report on Patentability and Applicant's Responses, Jul. 24, 2019.

Guo Zhi Kun, "Chapter 16: Cardiac Stem Cell," Atlas of Normal Cardiac Histology, 3rd Edition, (Chinese Edition), Henan Science and Technology Press, Feb. 1, 2015, pp. 153-154. ISBN: 978-7534975264.

SERVA Electrophoresis GmbH, "Collagenase NB 4 Standard Grade" https://www.serva.de/enDE/ProductDetails/6667_DS17454_Collagenase_NB_4_Standard_Grade_0_14.html retrieved Feb. 20, 2023.

Yu Yuanxun et al, Molecular Cardiology of China, (Chinese Edition), Anhui Science and Technology Press, Aug. 1, 2015, p. 324 ISBN: 978-7533766368.

Wu Yan Feng et al, Practical Medical Cell Culture Technology, (Chinese Edition), Sun Yat-sen Pub. Date :Jan. 1, 2010 version 1, 2000, p. 330 ISBN: 978-7306035806.

Karl-Ludwig Laugwitz et al, "Postnatal isl1+ cardioblasts enter fully differentiated cardiomyocyte lineages," Nature, Feb. 10, 2005, vol. 433, No. 7026, pp. 647-653.

* cited by examiner

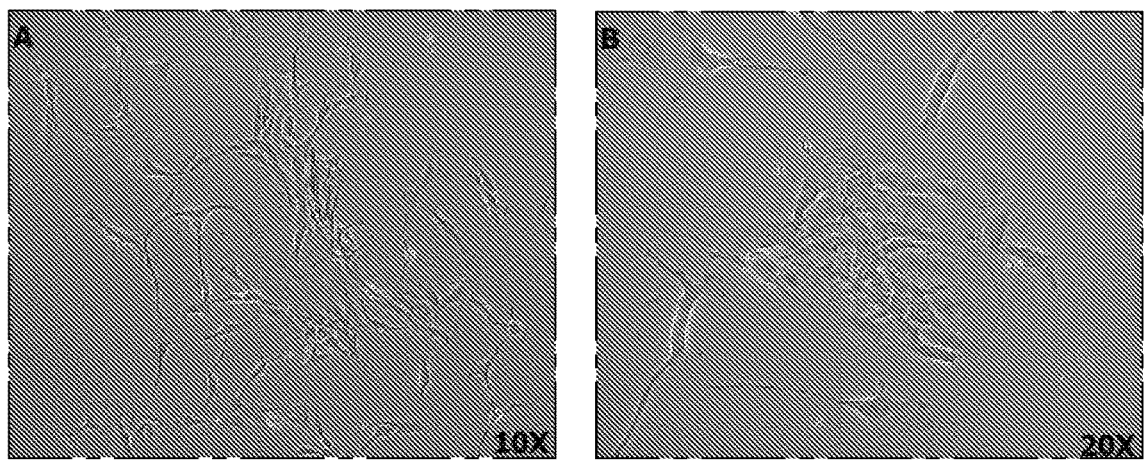
FIG.5
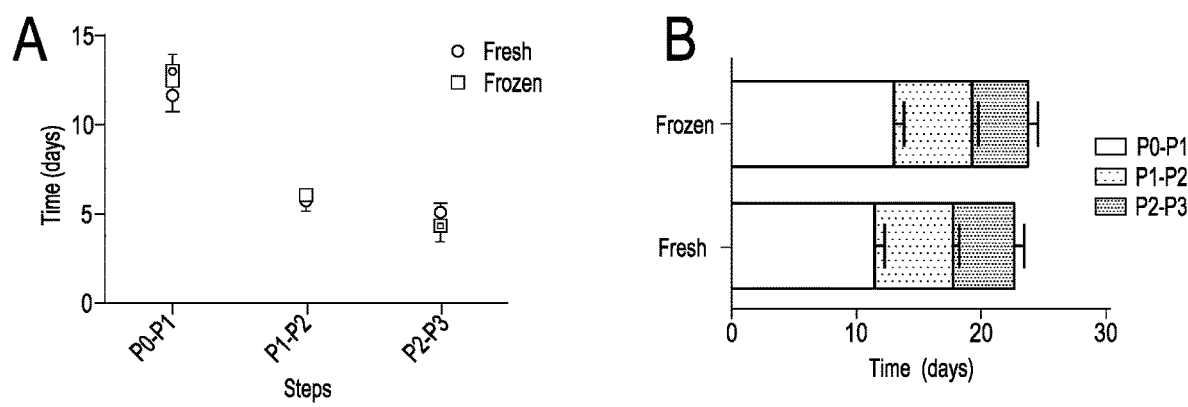
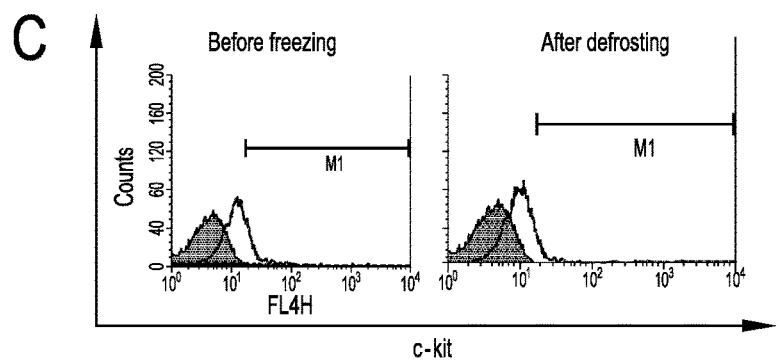
FIG.6

FIG.7
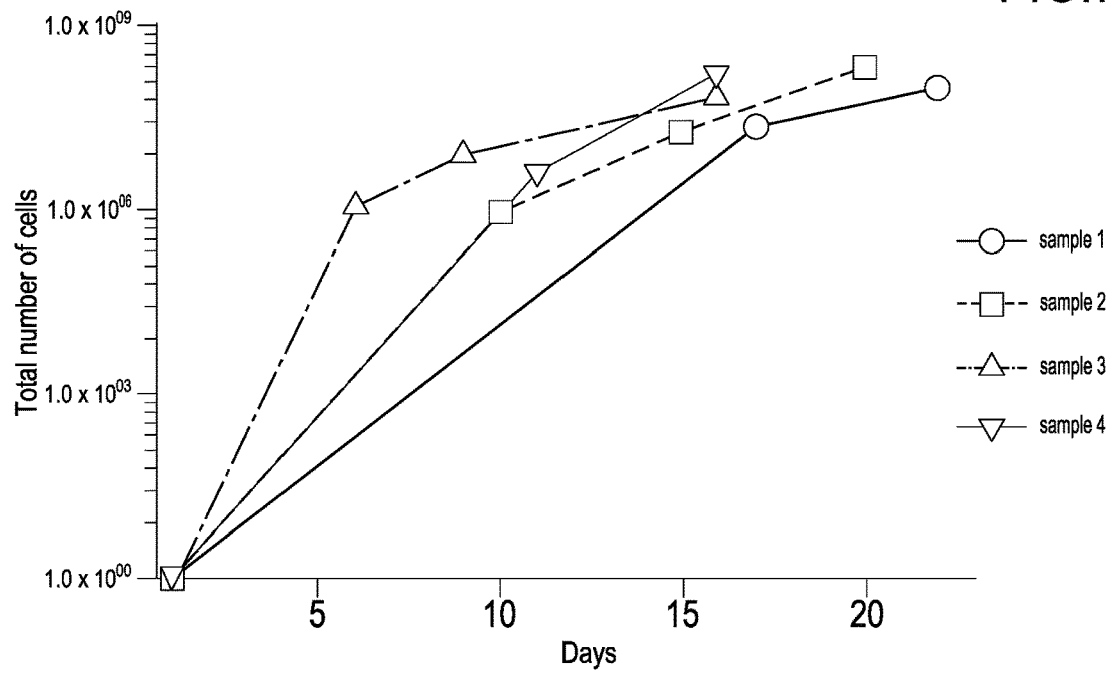
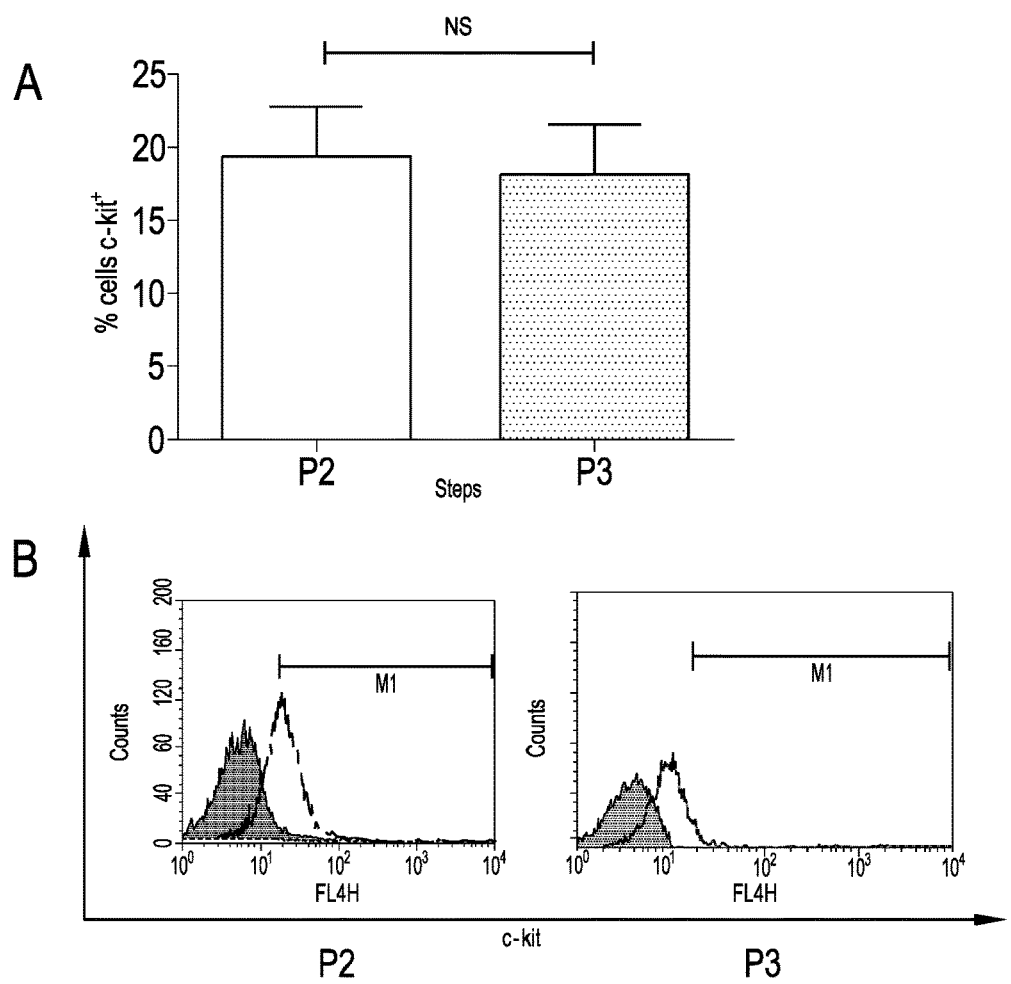
FIG.8

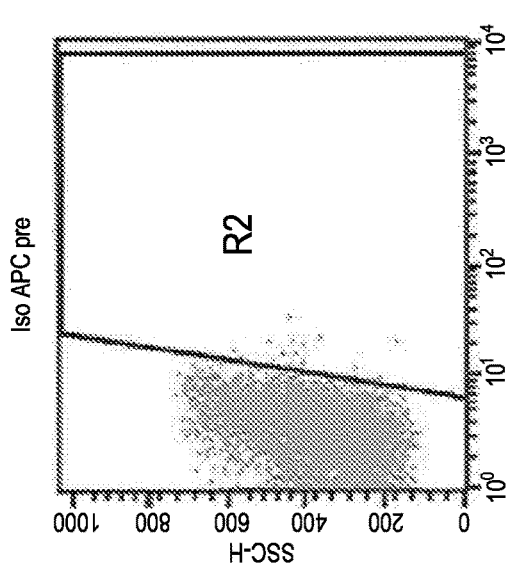
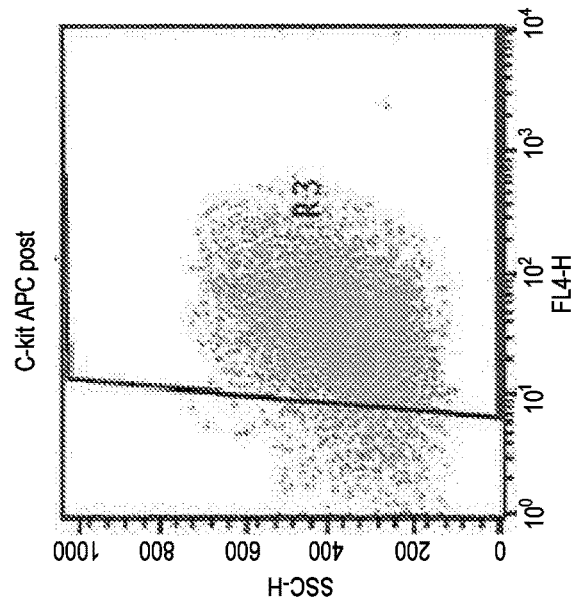
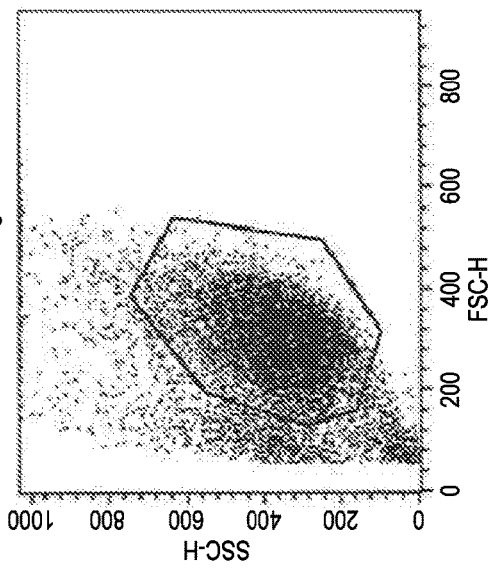
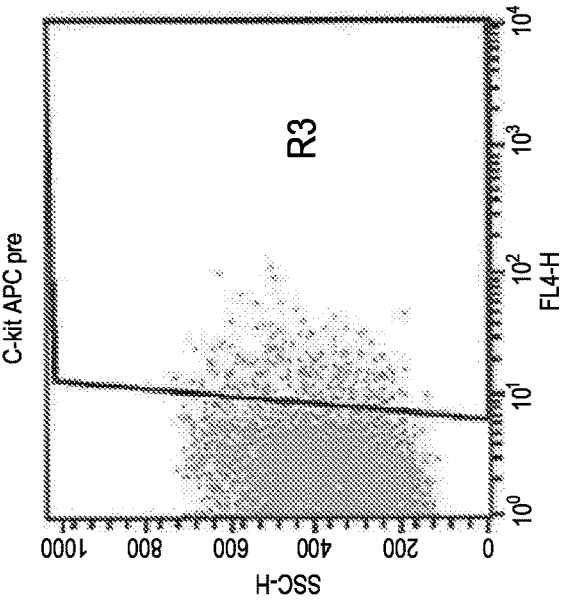
FIG. 9

| | | | | |
|---|---|---|---|---|
| CD1a | CD55 | CD132 | CD235ab | CLEC9A |
| CD1b | CD56 (NCAM) | CD134 | CD243 | CX3CR1 |
| CD1c | CD57 | CD131 | CD244 (2B4) | CXCR7 |
| CD1d | CD58 | CD137 (4-1 BB) | CD245 (p220/240) | delta-Opioid receptor |
| CD2 | CD59 | CD137L (4-1 BB Ligand) | CD252 (OX4OL) | DLL1 |
| CD3 | CD61 | CD138 | CD253 (TRAIL) | DLL4 |
| CD4 | CD62E | CD140a | CD254 | DR3 (TRAMP) |
| CD5 | CD62L | CD140b | CD255 (TWEAK) | EGFR |
| CD6 | CD62P P-Selectin | CD141 | CD257 (BAFF,BLYS) | erbB3/HER-3 |
| CD7 | CD63 | CD143 | CD258 (LIGHT) | FceR1 Alpha |
| CD8a | CD64 | CD143 | CD261 (DR4, TRAIL-R1) | FcRL6 |
| CD9 | CD66a/c/e | CD146 | CD262 (DR5, TRAIL-R2) | |
| CD10 | CD66b | CD148 | CD263 (DcR1, TRAIL-R3) | GARP (LRRC32) |
| CD11a | CD69 | CD150 (SLAM) | CD266 (Fn14, Recettore TWEAK) | HLA -A,B,C |
| CD11b | CD70 | CD152 | CD267 (TACI) | HLA -A2 |
| CD11b | CD71 | CD154 | CD268 (BAFF-R, BAFFR) | HLA -DQ |
| CD11c | CD73 | CD155 (PVR) | CD270 (HVEM) | HLA -DR |
| CD13 | CD74 | CD156c (ADAM10) | CD271 | HLA -E |
| CD14 | CD79b | CD158a/h | CD273 (B7-DC, PD-L2) | HLA -G |
| CD15 (SSEA -1) | CD80 | CD158b (KIR2DL2/L3, NKAT2) | CD274 (B7-H1, PD-L1) | IFN-g R b chain |
| CD16 | CD81 | CD158d | CD275 (B7-H2,B7-RP1, ICOSL) | Ig K light chain |
| CD18 | CD82 | CD158e1 (KIR3DL1, NKB1) | CD276 | Ig omega light chain |
| CD19 | CD83 | CD158f | CD277 | IgD |
| CD20 | CD84 | CD161 | CD278 (ICOS) | IgM |
| CD21 | CD85a (ILT5) | CD162 | CD279 (PD-1) | IL-28RA |
| CD22 | CD85d (ILT4) | CD163 | CD282 (TLR2) | Integrin alpha 9 beta1 |
| CD23 | CD85g (ILT7) | CD164 | CD284 (TLR4) | Integrin beta5 |
| CD24 | CD85h (ILT1) | CD165 | CD286 (TLR6) | Integrin beta7 |
| CD25 | CD85j (ILT2) | CD166 | CD290 | Jagged 2 |
| CD26 | CD85k (ILT3) | CD167a (DDR1) | CD294 | LAP |
| CD27 | CD86 | CD169 | CD298 | Lymphotoxin beta receptor |
| CD28 | CD87 | CD170 (Siglec-5) | CD300e (IREM-2) | Mac-2 (Galectin-9) |
| CD29 | CD88 | CD172a (SIRPa) | CD300F | MAIR-II |
| CD30 | CD89 | CD172b (SIRPg) | CD301 | MICA/MICB PE |
| CD31 | CD90 (Thy1) | CD172g (SIRPg) | CD303 | MSC (W3D5) |
| CD32 | CD67 | CD178 (Fas-L) | CD304 | MSC (W5C5) |
| CD33 | CD94 | CD179a | CD307 | MSC (W7C6) |
| CD34 | CD95 | CD179b | CD307d (FcRL4) | MSC e NPC (W4A5) |
| CD35 | CD96 | CD180 (RP105) | CD314 (NKG2D) | MSCA-1 (MSC,W8B2) |
| CD36 | CD97 | CD181 (CXCR1) | CD317 | NKp80 |
| CD38 | CD98 | CD182 (CXCR2) | CD318 (CDC1) | Notch1 |
| CD39 | CD100 | CD183 | CD319 (CRACC) | Notch2 |
| CD40 | CD101 (BB27) | CD184 (CXCR4) | CD317 (E-Cadherin) | Notch3 |
| CD41 | CD102 | CD193 (CCR3) | CD325 | Notch4 |
| CD42b | CD103 | CD195 (CCR5) | CD326 (Ep-CAM) | NPC (57D2) |
| CD43 | CD104 | CD196 | CD328 (Siglec-7) | Podoplanin |
| CD44 | CD105 | CD197 (CCR7) | CD334 (FGFR4) | Pre- BCR |
| CD45 | CD106 | CD200 (OX2) | CD335 (NKp46) | PSMA |
| CD45RA | CD107a (LAMP-1) | CD200 R | CD336 (NKp44) | Siglec-10 |
| CD40RB | CD108 | CD201 (EPCR) | CD337 (NKp30) | Siglec- 8 |
| CD40RO | CD109 | CD202b (Tie2/Tek) | CD338 (ABCG2) | Siglec- 9 |
| CD46 | CD111 | CD203c (E-NPP3) | CD340 (erbB2 HER-2) | SSEA-1 |
| CD47 | CD112 (Nectin -2) | CD205 (DEC-205) | CD344 (Frizzled-4) | SSEA-3 |
| CD48 | CD114 | CD206 (MMR) | CD351 | SSEA-4 |
| CD49a | CD115 | CD207 (Langerin) | CD352 (NTB-A) | SSEA-5 |
| CD49c | CD116 | CD209 (DC-SIGN) | CD354 (TREM-1) | TCRg/d |
| CD49d | CD117 (c- kit) | CD210 (IL-10 R) | CD355 (CRTAM) | TCR Vbeta13.2 |
| CD49e | CD119 | CD213a2 | CD357 (GITR) | TCR Vbeta23 |
| CD49e | CD122 | CD215 (IL - 15 R alpha) | CD360 (IL-21R) | TCR Vbeta6 |
| CD50 (ICAM-3) | CD123 | CD218a (IL - 18R alpha) | Microglobulin beta 2 | TCR Vbeta9 |
| CD51 | CD124 | CD220 | BTLA | TCR Vdelta2 |
| CD51/61 | CD126 | CD221 (IGF- 1R) | C3AR | TCR Vg9 |
| CD52 | CD127 (IL 7 R alpha) | CD226 (DNAM-1) | C5L2 | |
| CD53 | CD129 (IL-9 R) | CD229 (Ly-9) | CCR10 | |
| CD54 | CD131 | CD221 (TALLA) | CLEC12A | |

FIG.17

METHOD FOR THE ISOLATION OF SUBPOPULATIONS OF CARDIAC PROGENITOR CELLS AND RELATED USES IN THE MEDICAL FIELD

The present invention relates to a method for the isolation of subpopulations of cardiac progenitor cells from a heart tissue sample, the population thus obtained and the related uses in the medical field for the cell therapy or cardiac cell and/or tissue transplantation field.

Progenitors are all cell populations that have the ability to proliferate and differentiate, also performing a support function for surrounding cells and tissues.

Progenitors are rare cells located in the tissues of living beings in order to perpetuate their functionality through the exchange of damaged cells. They were initially discovered in tissues with the highest cell exchange such as bone marrow and epithelial tissue, but it is now well known that there is a population of progenitor cells living in different tissues, also with reduced regenerative ability.

The discovery of the progenitors resident in the adult heart has revolutionized the dogma of the heart as an organ incapable of self-renewal.

This discovery has led to studies on resident cardiac progenitors with the aim of developing therapy able to regenerate the myocardium after ischemic or other damage. Different types of cells, characterized by different surface markers have been proposed and studied and some have been tested in phase I, and some phase II, clinical trials initially approved by the FDA in the USA and more recently also in the rest of the world, but not in Italy as yet.

Such knowledge of cardiac progenitors has widened research horizons in order to introduce innovative therapies within what is defined as regenerative medicine.

The use of stem cells (including resident cardiac progenitors) for clinical trials must follow rigorous criteria. They ensure that the translation of stem cells is performed according to the same regulatory standards used for the production of medicines.

Good Manufacturing Practices (GMPs) are guidelines for the production of medicines according to the current reference pharmacopoeia (American, European, etc.). In Italy, the phase I clinical trial for cell therapy products (CTPs) is subject to the prior opinion of the Italian Institute of Health (ISS). From the perspective of possible clinical use of cardiac progenitors it is therefore fundamental to develop and validate the procedures for preparing them with reference to the GMPs in accordance with the 2004 guidelines of the ISS on CTPs.

The isolating protocols available in the art (see ref. [4], [5], [6]) allow isolating cardiac progenitors populations (CD117+) using a magnetic selection system to research scope. In fact, in order to select the population of cardiac progenitors using the magnetic selection system for GMP productions and clinical trials it is necessary first of all to extensively expand the unselected starting population whose selection is desired. The selection system having research scope allows the selection starting from a number of cells of about $1\times10^6$, $1\times10^7$, while the GMP-grade selection system which is nowadays available is not working starting from such a small number of starting cells. In order to make the immunomagnetic selection system working it is necessary to select a starting cell number of about $1\times10^9$ (peripheral or marrow blood cells), that is the first mandatory condition to select a progenitor population under GMP-grade conditions is adopting a strategy to maximize the selectable starting population approaching the amount of $1\times10^9$ cells.

Therefore, to date, there is no method on the market for the production of cardiac progenitors that can be used in clinical trials in Italy where the ISS already requires GMP production levels for phase I studies, like the legislation for the production of medicines.

From the perspective of the cell therapy in the cardiovascular field, the cell type covers a fundamental role for therapeutic success. By analysing the cardiac tissue as a source three different types of cells have currently been proposed, already tested in phase I clinical trials and some in phase II.

In particular:
1) the population of cardiac stem cells (CSCs), selected for the surface expression of CD117 antigen, c-kit [1];
2) cardiosphere-derived cells (CDCs), not isolated by a marker, but for their ability to form spherical aggregates [2];
3) phase I studies and trials that use a combined therapy approach through the use of a combination of CSC-ckit+ cells and bone marrow mesenchymal stem cells (MSCs) [3].

All three types of cells listed above have advantages and disadvantages according to the type of cell and the manufacturing technique that allows them to be obtained.

For example, the cardiosphere-derived cell population not selected by any marker (CDCs) has the advantage of being easy to obtain in large quantities, but the disadvantage of being a heterogeneous population that is not clearly characterized. On the other hand, the CSC population has the advantage of being enriched with very well characterized stem cells/progenitors and the proven therapeutic function in terms of functional increase of the myocardium and the quality of life of the patients treated; however, the aforementioned population displays the disadvantage of being an extremely rare endogenous population, with reduced proliferation capacities therefore difficult to obtain in a clinically significant number.

The latest approach currently available (combination of CSCs and MSCs) could potentially have a better therapeutic advantage as the combinations of cells could produce better results, but at the same time the mechanism underlying the possible improvement remains unclear; furthermore, the cell combination introduces variability in the determination of the efficacy ratios and the most active population in the damaged myocardium.

The authors of the present invention have now developed a method for the isolation of human cardiac progenitor cell subpopulations (hCPCs) that allows the different technical problems affecting the isolation processes of the background to be solved, particularly in terms of efficiency in obtaining a clinically significant number of hCPCs and high purity standards.

In fact, the method for the isolation of cardiac progenitors according to the invention allows different subpopulations of cardiac cells to be expanded in a controlled way from the primary culture, maintaining their phenotypic characteristics and obtaining a clinically significant number of cells in rather reduced time frames.

Another objective of the method according to the invention is that of isolating cells from any biopsy coming from any heart source (solely by way of example, the left and right auricle, septum, apex, ventricular biopsy) even starting from a tiny amount of starting material.

The isolation method according to the invention is also advantageous as it is extremely versatile, i.e. adapted for the selection of any subpopulation present in the original population that positively and/or negatively expresses a surface antigen, also in GMP conditions. GMP (Good Manufacturing Practice) conditions mean a level of development according to good manufacturing practices: protocol/reagent/substance tested using reagents, tools and technical expedients that allow the production to be carried out in a pharmaceutical workshop authorized for the production of a potential clinical batch (e.g. within a clinical protocol).

The highly selected subpopulation thus isolated in a clinically significant number can be discriminated through positive or negative selection (or both) of surface markers, through detection with specific antibodies.

The therapeutic sector of interest of the population of cells that can be obtained with the isolation method of the present invention is, by way of non-limiting example, heart diseases that currently have no effective treatment.

Through the method for the isolation of the population of progenitor cells according to the present invention it is therefore possible to extend the therapeutic application of cardiac progenitors to a large number of subjects. In particular, the present method offers the possibility to obtain an extremely versatile cell therapy instrument for advanced heart failure (of ischemic and non-ischemic origin) and refractory ischemic cardiomyopathy. The method is further applicable in both an autologous and allogeneic cell therapy context, considering the maintained cell identity following cryo-conservation.

Therefore, the subject matter of the present invention is a method for the isolation of subpopulations of human cardiac progenitor cells (hCPCs) comprising the following steps:
  a) mincing a heart tissue sample containing a population of cardiac cells;
  b) 4 times progressive digestion of the cardiac tissue with an enzymatic mixture until a cell suspension is achieved and filtration through filters of size comprised between 30 µm and 100 µm;
  c) further digestion of residual cardiac tissue obtained in step b) for 16 hours with an enzymatic mixture until a cell suspension is achieved and filtration through filters of size comprised between 30 µm and 100 µm;
  d) culturing the cell suspension obtained in step b) and c) in a culture medium suitable to propagate the cardiac cells;
  e) preliminary expansion the cell suspension obtained in step d) in a culture medium suitable to expand the cardiac cells in the presence of an enzymatic or non enzymatic solution;
  f) secondary expansion of the cardiac cells obtained in step e) in a culture medium suitable f) to further expand the cardiac cells in the presence of an enzymatic or non enzymatic solution;
  g) isolating one or more subpopulations of cardiac cells by positive and/or negative selection by the use of monoclonal antibodies directed against one or more surface antigens expressed in the starting population of cardiac progenitor cells.

Preferably said isolating step is carried out by immunomagnetic sorting.

The sample of heart tissue of step a) may come from any region of the cardiac organ and its annexes containing progenitor cells, either from fresh or frozen tissue. In a particularly preferred embodiment, said heart tissue sample is a bioptic sample.

Preferably, said heart tissue sample contains a primary population of cardiac cells from the right auricle, left auricle, septum, apex or ventricular biopsy (see FIG. 3). Even more preferably, the heart tissue sample is from the right auricle.

According to alternative embodiments of the aforementioned method, the starting heart tissue sample can come indifferently from adult subjects, children or foetuses.

The mincing step of step a) can occur in manual or automatic mode. The manual mode envisages the use of tweezers or surgical scissors in sterile conditions.

Step b) can be performed in four enzymatic digestion steps in order to obtain a viable cell suspension (4×30' digestion). Step c) allows to complete the digestion of the residual cardiac tissue obtained in step b) and maximize the number of in vitro expandable viable cells under GMP conditions. Preferably the 16-hours digestion of step b) is carried out overnight (O/N). FIG. 4 shows the comparison of the cells obtained after 4×30' digestion step of the cardiac tissue employed in the methods previously used by the inventors (see references [4] and [5]) alone or in combination with the complete digestion of the cardiac tissue fragment obtained adding a further 16 hours digestion. The treatment according to the invention allows to double the cell number obtained at the end of step b) (passage P0-P1).

The enzymatic digestion of step b and c) preferably takes place with an enzymatic mixture comprising a basal medium, preferably Ham's/F12, and an enzymatic solution. Preferably, said enzymatic solution comprises a mixture of collagenases and/or proteases. Even more preferably, said mixture of collagenases and/or proteases comprises one or more enzymes selected from collagenase I, collagenase II, collagenase IV, trypsin, accutase, collagenase A, dispase and liberase (i.e. NB4 or NB6 (GMP), Serva) or ethylenediaminetetraacetic acid (EDTA).

Preferably, the ideal medium for multiplying and expanding the cardiac cells in step d), e) and f)) comprises a basal medium, preferably Ham's/F12, serum, preferably 10% fetal bovine serum (FBS), other factors necessary for cell growth, specifically 2 mM L-glutathione, $5 \times 10^{-3}$ U/ml of human erythropoietin, 10 ng/ml of basic fibroblast growth factor (bFGF or FGF2) and antibiotics, specifically penicillin up to 1000 U/ml and streptomycin up to 1000 µg/ml. This medium is indicated below as F12H. The initials F12G indicates the same medium but used in GMP conditions.

Alternatively, it is also possible to use other media for the growth of the cardiac cell populations, in particular the basal medium can be selected from the group consisting of MEM, DMEM, Medium199, DMEM/F12, IMDM, neurobasal medium, EBM-2, α-MEM, mesencult or HCSCEM. Alternatively to bovine serum, horse serum can also be used. As further additional or alternative growth factors it is possible to use endothelial growth factor (EGF), leukemia inhibitory factor (LIF), sodium selenite, insulin, ascorbic acid, heparin, hydrocortisone, transferrin, 2-mercaptoethanol, L-glutamate, B27, transforming growth factor-beta 1, bone morphogenetic protein 2 (BMP-2) and bone morphogenetic protein 4 (BMP-4), insulin-like growth factor (IGF-1 and IGF-2), activin A, cardiotrophin-1, bovine brain extract (BBE) and thrombin. As antibiotics, gentamicin and amphotericin B can alternatively be used.

Furthermore, as an alternative to plastic for cell cultures, it is also possible to grow the cells on different plastics or on different supports, such as polylysine, fibronectin or porcine gelatin.

According to a particularly preferred embodiment, said enzymatic mixture comprises Ham's/F12 basal medium and the mixture of collagenase NB4 or NB6 Serva.

Preferably, said mixture of collagenase is present in a concentration comprised between 0.1 and 3 mg/ml.

Thanks to the complete enzymatic digestion of the bioptic sample, the aforementioned method allows the extraction of cells and cell clones more quickly and efficiently with respect to known protocols.

The cell suspension double expansion steps e) and f can be performed in one or more steps maintaining the expression of the main surface markers through the use of an enzymatic or non enzymatic solution that does not damage the cell membrane. Preferably, said enzymatic or non enzymatic solution is selected from the group that consists of TrypLE™ Select, a mixture of trypsin and/or EDTA, cell dissociation buffer (GIBCO), accutase or dispase.

Preferably, the suitable culture medium for expanding the cardiac cells is F12H as described above.

The cell population obtained from the primary culture of step c) can be cryo-conserved by maintaining the expression of the main surface markers.

It is commonly considered that non-embryonic progenitor/stem cells grow very slowly in medium and that it is necessary to separate them from differentiated cells, to prevent undesired dilutions and/or differentiations.

Thanks to the method according to the present invention, the cardiac stem and progenitor cells grow more quickly when they are maintained in a mixed population of differentiated cells.

With this new procedural expedient which envisages a preliminary and a secondary expansion step—unlike the methods known in the background (see ref. [1], [4], [5])—it is possible to massively expand the progenitor subpopulation of interest before the final cell isolation process (see FIG. 7) and to enhance the final purity.

This additional expansion step allows to obtain at least 10 times the number of starting cells in comparison to the prior art (rif. [4], FIG. 7), considering as starting material a fragment of auricle of average weight of 141.4±28.29 mg and allowing to select the population of interest also in GMP-grade conditions (see Example 4).

Another advantage due to the increasing number of starting cells before selection is that the method of the invention does not require further post-selection expansion steps of the selected cells because the obtained number is already sufficient to be employed in clinical trials of cell therapy (considering the number of cells injected in the clinical trial in this sector). This leads to another advantage in terms of "quality", because by avoiding post-selection expansion step it is possible to prevent the dilution of the selected population of interest, which, as known from the literature, is not expandable as such because the culture has the intrinsic problem of the partial differentiation of the population itself.

The isolation of the population of interest can therefore be obtained starting from a much larger number of cells (at least 10 times with respect to the state of the art), therefore isolating a significantly high number of selected progenitor cells.

The method based on the isolation of a population through the use of specific antibodies that recognize a surface antigen, makes it possible to isolate any cardiac cell subpopulation, even rare, thanks to a signal amplification system.

The proposed method is a decisively quicker method (on average 22 days) with respect to others used for obtaining a similar cell population (see FIG. 6b). In fact, the state of the art shows that an average of 66.5 days are necessary for obtaining a decisively lower quality cell product (in terms of number and purity).

Therefore, the method according to the present invention allows one or more cardiac cell subpopulations to be obtained with high purity for one or more selected surface markers, as well as a clinically significant quantity of cells.

The specific antibodies used in the isolation step g) of the method according to the invention are preferably marked monoclonal antibodies (e.g. with biotin), more preferably marked with a fluorescent molecule.

Preferably said fluorescent molecule is selected from fluorescein (FITC), allophycocyanin (APC) or another fluorescent marker suitable to be combined with a magnetic selection system. It is possible to perform direct or indirect marking of the aforementioned antibodies.

Furthermore, said antibodies can be primary or secondary (only for indirect marking).

According to a preferred embodiment, the separation according to step g) is an immunomagnetic separation and the monoclonal antibodies are coupled to magnetic beads.

Alternative possible selection systems that can be used to carry out the separation according to step g) according to the invention are Dynabeads Magnetic Separation Technology Thermo Fisher Scientific, EasySep™ Magnet STEMCELL or flow cytometry cell Sorting (i.e. FacsAria BD).

According to a preferred embodiment of the method, when the cardiac tissue sample comes from the right auricle or the septum (see subsequent Example 5 of characterization using FACS analysis) it is possible to use monoclonal antibodies optionally marked with a fluorescent marker preferably selected from biotin, FITC and APC, directed against one or more antigens selected from the group of antigens listed in the following Table 1:

TABLE 1

| CD1a | CD1b | CD1c | CD1d | CD2 |
|---|---|---|---|---|
| CD3 | CD4 | CD5 | CD6 | CD7 |
| CD8a | CD9 | CD10 | CD11a | CD11b |
| CD11b activated | CD11c | CD13 | CD14 | CD15 (SSEA-1) |
| CD16 | CD18 | CD19 | CD20 | CD21 |
| CD22 | CD23 | CD24 | CD25 | CD26 |
| CD27 | CD28 | CD29 | CD30 | CD31 |
| CD32 | CD33 | CD34 | CD35 | CD36 |
| CD38 | CD39 | CD40 | CD41 | CD42b |
| CD43 | CD44 | CD45 | CD45RA | CD45RB |
| CD45RO | CD46 | CD47 | CD48 | CD49a |
| CD49c | CD49d | CD49e | CD49f | CD50 (ICAM-3) |
| CD51 | CD51/61 | CD52 | CD53 | CD54 |
| CD55 | CD56 (NCAM) | CD57 | CD58 | CD59 |
| CD61 | CD62E | CD62L | CD62P (P-Selectin) | CD63 |
| CD64 | CD66a/c/e | CD66b | CD69 | CD70 |
| CD71 | CD73 | CD74 | CD79b | CD80 |
| CD81 | CD82 | CD83 | CD84 | CD85a (ILT5) |
| CD85d (ILT4) | CD85g (ILT7) | CD85h (ILT1) | CD85j (ILT2) | CD85k (ILT3) |

TABLE 1-continued

| | | | | |
|---|---|---|---|---|
| CD86 | CD87 | CD88 | CD89 | CD90 (Thy1) |
| CD93 | CD94 | CD95 | CD96 | CD97 |
| CD99 | CD100 | CD101 (BB27) | CD102 | CD103 |
| CD104 | CD105 | CD106 | CD107a (LAMP-1) | CD108 |
| CD109 | CD111 | CD112 (Nectin-2) | CD114 | CD115 |
| CD116 | CD117 (c-kit) | CD119 (IFN-g R alpha chain) | CD122 | CD123 |
| CD124 | CD126 (IL-6 R alpha) | CD127 (IL7 R alpha) | CD129 (IL-9 R) | CD131 |
| CD132 | CD134 | CD135 | CD137 (4-1 BB) | CD137L (4-1 BB Ligand) |
| CD138 | CD140a | CD140b | CD141 | CD143 |
| CD143 | CD146 | CD148 | CD150 (SLAM) | CD152 |
| CD154 | CD155 (PVR) | CD156c (ADAM10) | CD158a/h | CD158b (KIR2DL2/L3, NKAT2) |
| CD158d | CD158e1 (KIR3DL1, NKB1) | CD158F | CD161 | CD162 |
| CD163 | CD164 | CD165 | CD166 | CD167a (DDR1) |
| CD169 | CD170 (Siglec-5) | CD172a (SIRPa) | CD172b (SIRPg) | CD172g (SIRPg) |
| CD178 (Fas-L) | CD179a | CD179b | CD180 (RP105) | CD181 (CXCR1) |
| CD182 (CXCR2) | CD183 | CD184 (CXCR4) | CD193 (CCR3) | CD195 (CCR5) |
| CD196 | CD197 (CCR7) | CD200 (OX2) | CD200 R | CD201 (EPCR) |
| CD202b (Tie2/Tek) | CD203c (E-NPP3) | CD205 (DEC-205) | CD206 (MMR) | CD207 (Langerin) |
| CD209 (DC-SIGN) | CD210 (IL-10 R) | CD213a2 | CD215 (IL-15 Ralpha) | CD218a (IL-18R alpha) |
| CD220 | CD221 (IGF-1R) | CD226 (DNAM-1) | CD229 (Ly-9) | CD231 (TALLA) |
| CD235ab | CD243 | CD244 (2B4) | CD245 (p220/240) | CD252 (OX4OL) |
| CD253 (Trail) | CD254 | CD255 (TWEAK) | CD257 (BAFF, BLYS) | CD258 (LIGHT) |
| CD261 (DR4, TRAIL-R1) | CD262 (DR5, TRAIL-R2) | CD263 (DcR1, TRAIL-R3) | CD266 (Fn14, TWEAK F | CD267 (TACI) |
| CD268 (BAFF-R, BAFFR) | CD270 (HVEM) | CD271 | CD273 (B7-DC,PD-L2) | CD274 (B7-H1,PD-L1) |
| CD275 (B7-H2, B7-RP1, ICOSL) | CD276 | CD277 | CD278 (ICOS) | CD279 (PD-1) |
| CD282 (TLR2) | CD284 (TLR4) | CD286 (TLR6) | CD290 | CD294 |
| CD298 | CD300e (IREM-2) | CD300F | CD301 | CD303 |
| CD304 | CD307 | CD307d (FcRL4) | CD314 (NKG2D) | CD317 |
| CD318 (CDCP1) | CD319 (CRACC) | CD324 (E-Cadherin) | CD325 | CD326 (Ep-CAM) |
| CD328 (Siglec-7) | CD334 (FGFR4) | CD335 (NKp46) | CD336 (NKp44) | CD337 (NKp30) |
| CD338 (ABCG2) | CD340 (erbB2_HER-2) | CD344 (Frizzled-4) | CD351 | CD352 (NTB-A) |
| CD354 (TREM-1) | CD355 (CRTAM) | CD357 (GITR) | CD360 (IL-21R) | beta2-microglobulin |
| BTLA | C3AR | C5L2 | CCR10 | CLEC12A |
| CLEC9A | CX3CR1 | CXCR7 | delta-Opioid Receptor | DLL1 |
| DLL4 | DR3 (TRAMP) | EGFR | erbB3/HER-3 | FceRIalpha |
| FcRL6 | Galectin-9 | GARP (LRRC32) | HLA-A, B, C | HLA-A2 |
| HLA-DQ | HLA-DR | HLA-E | HLA-G | IFN-g R b chain |
| Ig light chain k | Ig light chain omega | IgD | IgM | IL-28RA |
| Integrin alpha9beta1 | Integrin beta5 | Integrin beta7 | Jagged 2 | LAP |
| Lymphotoxin beta receptor(L | Mac-2 (Galectin-3) | MAIR-II | MICA/MICB PE | MSC(W3D5) |
| MSC(W5C5) | MSC(W7C6) | MSC and NPC(W4A5) | MSCA-1(MSC, W8B2) | NKp80 |
| Notch1 | Notch2 | Notch3 | Notch4 | NPC(57D2) |
| Podoplanin | Pre-BCR | PSMA | Siglec-10 | Siglec-8 |
| Siglec-9 | SSEA-1 | SSEA-3 | SSEA-4 | SSEA-5 |
| TCRg/d | TCR Vbeta13.2 | TCR Vbeta23 | TCR Vbeta8 | TCR Vbeta9 |
| TCR Vdelta2 | TCR Vg9 | TCR Valpha24-Jalpha18 | TCR Valpha7.2 | TCR alpha/beta |
| Tim-1 | Tim-3 | Tim-4 | TLT-2 | TRA-1-60R |
| TRA-1-81 | TSLPR (TSLP-R) | | | |

According to a preferred embodiment of the isolation method according to the invention the monoclonal antibodies to perform the positive and/or negative selection of the subpopulations of cardiac progenitor cells of interest according to step g) of the method according to the invention are anti-CD117 and/or anti-CD90.

Therefore, according to a preferred embodiment of the present invention refers to a subpopulation of human cardiac progenitor cells obtained through the isolation method outlined above characterized by a profile of surface antigens selected between CD90⁻ and CD117⁺/CD90⁻, according to whether negative selection (see Example 2) or simultaneous double positive and negative selection (see Example 3) are used. In particular, the subpopulation of human cardiac progenitor cells hCPC CD90⁻ showed high angiogenic and cardioprotective potential (see FIGS. 20-21), in addition to a significant anti-inflammatory effect (see FIG. 22). Also the subpopulation CD117⁺/CD90⁻ showed a significant anti-inflammatory effect (see FIG. 22). The reduced collagen production revealed by the hCPC CD90⁻ subpopulation render it a suitable candidate for transplant (see FIG. 23).

Therefore, a further object of the present invention is a subpopulation of human cardiac progenitor cells CD90⁻ and CD117⁺/CD90⁻, selected by the isolation method outlined above, for use in the medical field. The subpopulations obtainable through the isolation method of the present invention can be used alone or also in combination with each other or with other human cardiac progenitor cells subpopulations (e.g. CD117⁺, CD117⁻, CD90⁺, CD117⁺/CD90⁺, CD117⁻/CD90⁻ and CD117⁻/CD90⁺ subpopulations).

The invention further relates to the use of human cardiac cell subpopulations obtained through the isolation method outlined above in cardiovascular cell therapy or in the cardiac cell and/or tissue transplantation field.

The diseases that can benefit from the present invention include but are not limited to acute and chronic heart disease, diseases of ischemic or non-ischemic origin, myocardial diseases or lesions, cardiovascular diseases of genetic origin, congenital heart defects, valvular heart disease, arrhythmia including malignant forms, congestive and non-congestive heart failure, subendocardial fibrosis, left or right ventricular hypertrophy, dilation of the left ventricle, myocardial acute infarction, restenosis, myocarditis, idiopathic dilated cardiomyopathy, chronic ischemic cardiomyopathy, dystrophyc cardiomyopathy (e.g. Duchenne or Becker dystrophy), pericardial diseases and/or disorders, angina pectoris including refractory forms, diseases or disorders of the blood vessels (atherosclerosis, aneurysms, arterial inflammation, all diseases of the arteries, arterioles and capillaries and related structures, including narrowing of the peripheral arteries and critical ischemia of the lower limbs), hypertension, autoimmune diseases.

Heart protection, immunoregulatory capacity and the cardiac regeneration potential of the cells selected with the aforementioned method according to the invention, make it a suitable instrument for the treatment of various diseases also including the wound repair processes or regeneration therapy.

The present invention will now be described, for non-limiting illustrative purposes, according to a preferred embodiment thereof, with particular reference to the attached figures, wherein:

FIG. 1, panels A) and B) show a view of the fragment of right auricle just harvested during aorta-coronary bypass surgery, before cleaning, weighing and mincing. Panels C) and D) show the two faces of the fragment after a longitudinal cut. Panel E) shows the fragments obtained after manual mincing. Panel F) illustrates a diagram showing the mean weight (expressed in mg of tissue) with the related standard deviation of the collected and processed auricle.

FIG. 5 shows the images obtained under the optical microscope of a primary culture in vitro 5 days after being cultured. Panel B) shows a clone, presumably generated from a single progenitor cell, very frequent in this type of culture.

FIG. 6, panel A) shows a diagram that illustrates the average time necessary for each step in the culture medium, comparing fresh and frozen samples, from which it appears clear how the technique can be reproduced in both cases without statistically significant variations to the growing times. Panel B) shows the sum of the days from the primary culture to the selection of the population of interest (P3) both in fresh and frozen processed samples, subdivided by steps. The possibility of freezing was also proved in relation to the maintenance of the phenotype of interest. Panel C) shows the diagrams that demonstrate the expression of the antigen c-kit (CD117) before and after freezing the non-selected population.

FIG. 7 shows a graph illustrating the number of cells obtained from the complete expansion of four samples of cardiac tissue (right auricle) until the end of step 2 (P2-P3).

FIG. 8 shows the cytofluorimetric analyses reporting the percentage of progenitor cells of interest during the different steps. Panel A) shows a graph that illustrates the maintenance of the percentage of c-kit (CD117) in the population not selected during steps P2 and P3. Panel B) comprises the diagrams that show the expression of the antigen c-kit in the culture steps P2 and P3.

FIG. 9 shows an example of positive selection for the antigen c-kit. The diagrams provided show said population identified by physical parameters, while the expression of the antigen of interest is highlighted using a fluorescent antibody. Panel A) comprises the diagrams that show the analysed population identified by physical parameters, while the expression of the antigen of interest is highlighted using a fluorescent antibody. Panel B) presents an image representing the marked population only with the isotype conjugated with APC before selection used as a negative control of the non-specific marking (inside gate R2); panel C) illustrates the expression of the marker of the population before selection (inside gate R3) and panel D) shows the selection of the positive population after selection (inside gate R3).

Figure 10:
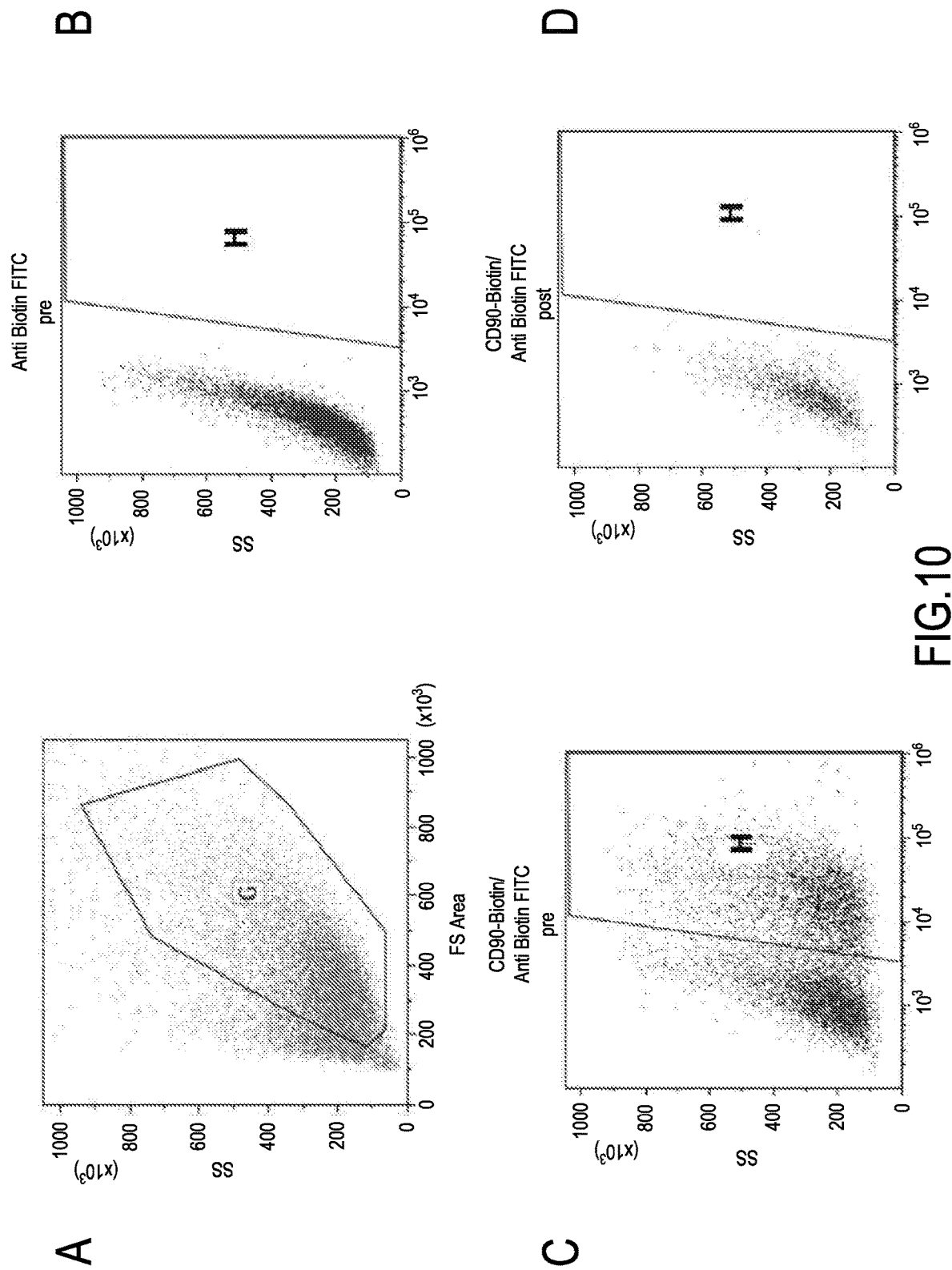

FIG. 10 shows an example of negative selection for the antigen CD90. The diagrams provided show the analysed population identified by physical parameters (panel A), while the expression of the antigen of interest is highlighted using a biotinylated antibody coupled to a secondary fluorescent antibody. Panel B) shows an image representing the population marked only with the secondary antibody (anti-Biotin marked with FITC) before selection (inside gate H). Panel C) shows the expression of the marker in the population before selection (inside gate H) and panel D) shows the selection of the negative population after selection (inside gate H).

Figure 11:
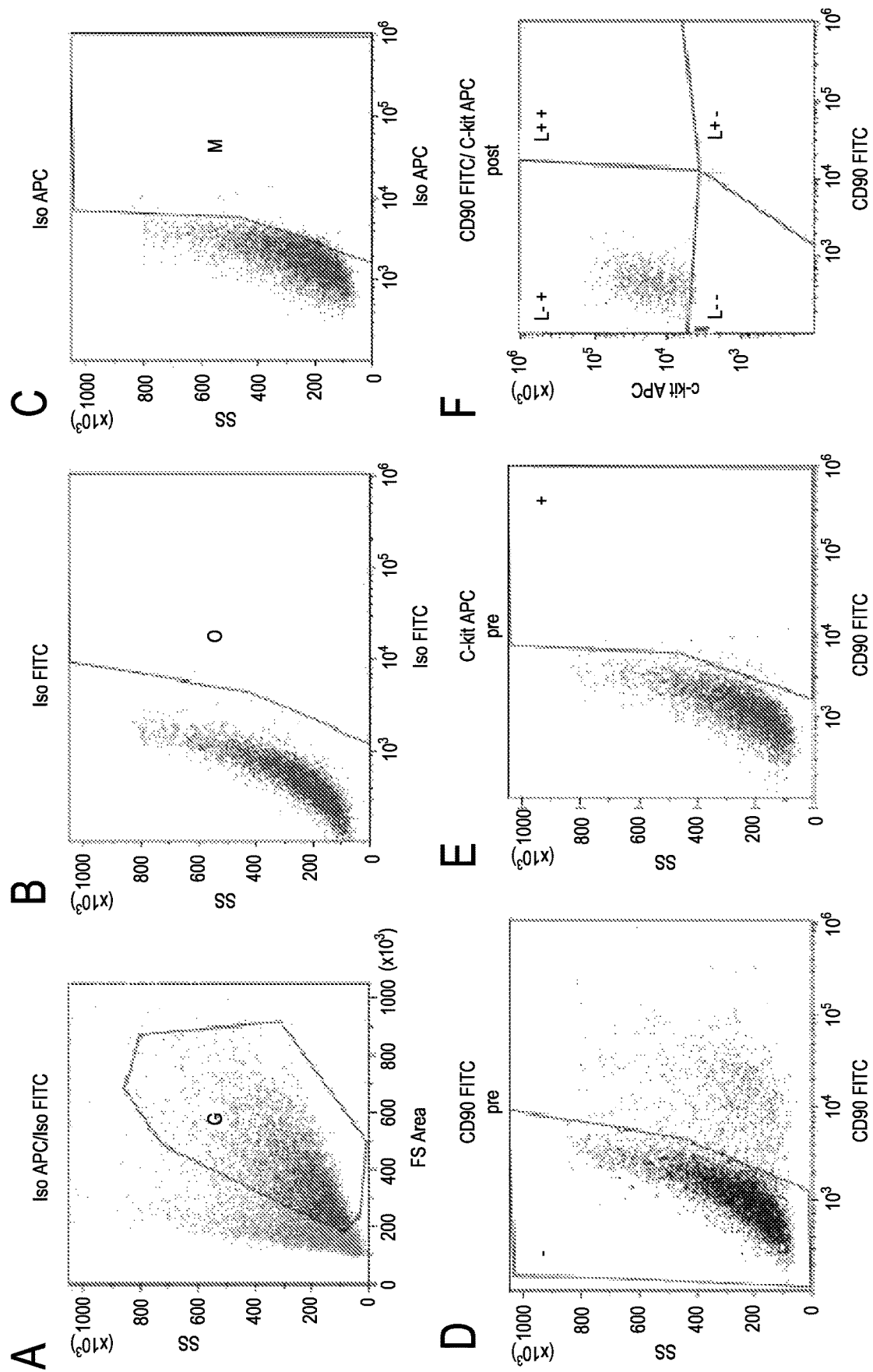

FIG. 11 shows an example of the double selection of a negative population for one marker (CD90) and positive for another marker (c-kit). The diagrams provided show the population analysed identified by physical parameters in panel A); panel B) presents an image representing the marked population only with the isotype conjugated with FITC before selection and APC (panel C) used as a negative control of the non-specific marking. Panels D) and E) show the expression of the antigens of interest CD90 conjugated to fluorochrome FITC (panel D) and c-kit conjugated to fluorochrome APC (panel E). In particular, panel D) shows the population of interest for negative selection (inside gate «−»); panel E) shows the population of interest for positive selection (inside gate «+») and panel F) shows the selection of the population identified by the expression of two markers after selection (inside gate «L−+»).

Figure 12:
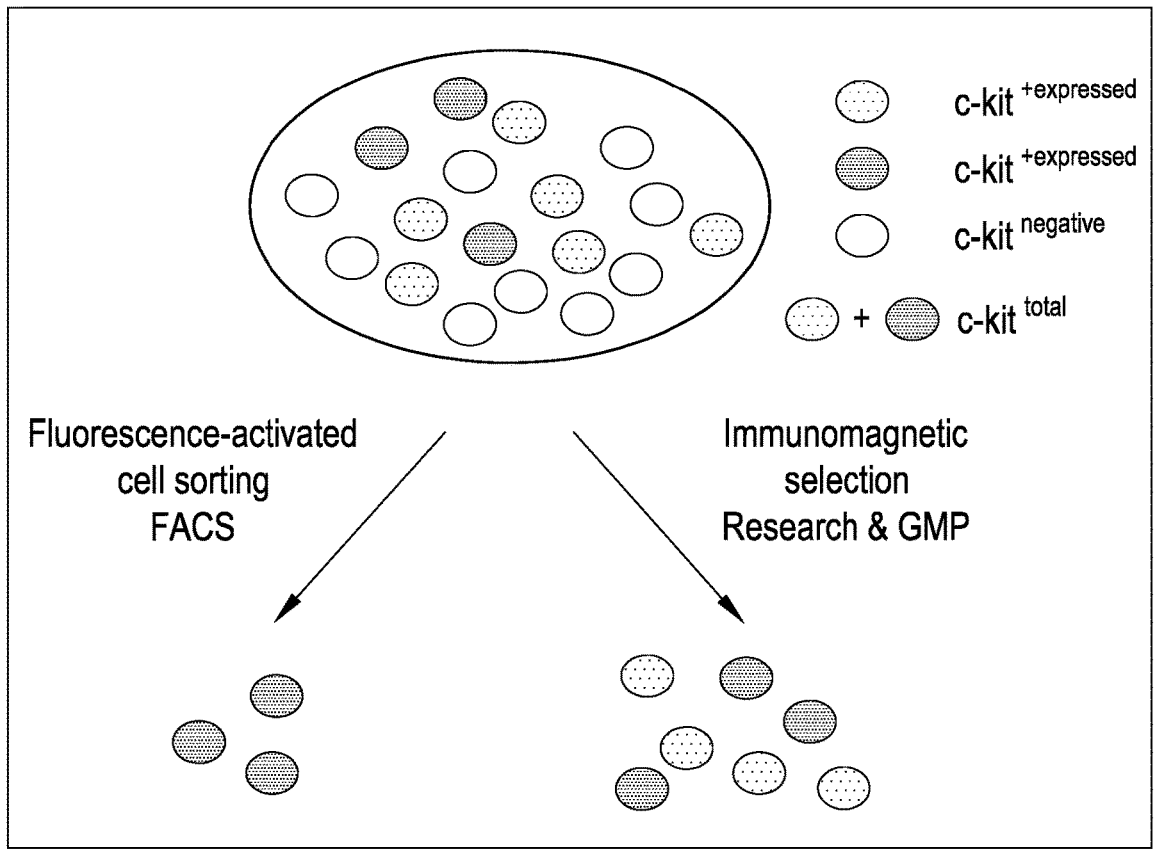

FIG. 12 illustrates a diagram of the isolation method according to the invention that also allows the population to be selected that expresses the antigen of interest (c-kit) characterized by an intermediate or low mean fluorescence intensity (panel A). Panel B) shows a table comparing the number of cells, the purity and the cell viability, of the cell population obtained with the method according to the invention with respect to the prior art [4].

Figure 13:
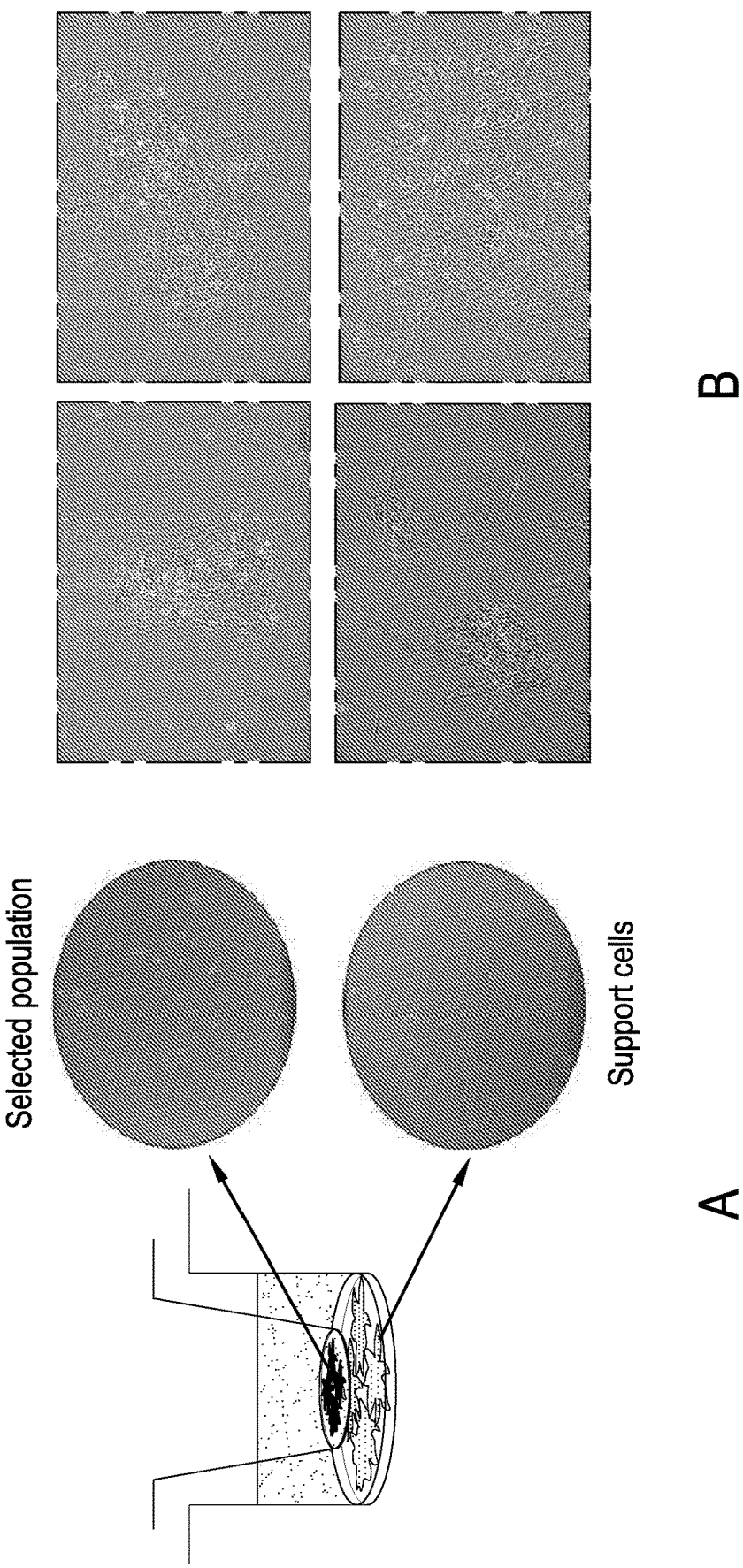

FIG. 13, panel A) shows a diagram of the process of seeding cells in a plate equipped with Transwell® culture inserts that allow the simultaneous growing of different cell types that are physically separated but share the same culture medium for possible growing after selection. In the case exemplified the selected cells are plated inside the Transwell® inserts in the upper chamber and the supported cells are plated in the lower chamber. Panel B) shows some examples of cultures of the selected cells. When placed back in culture the cells are viable and start growing again, also forming clones (a peculiar characteristic of progenitor/stem cells).

Figure 14:
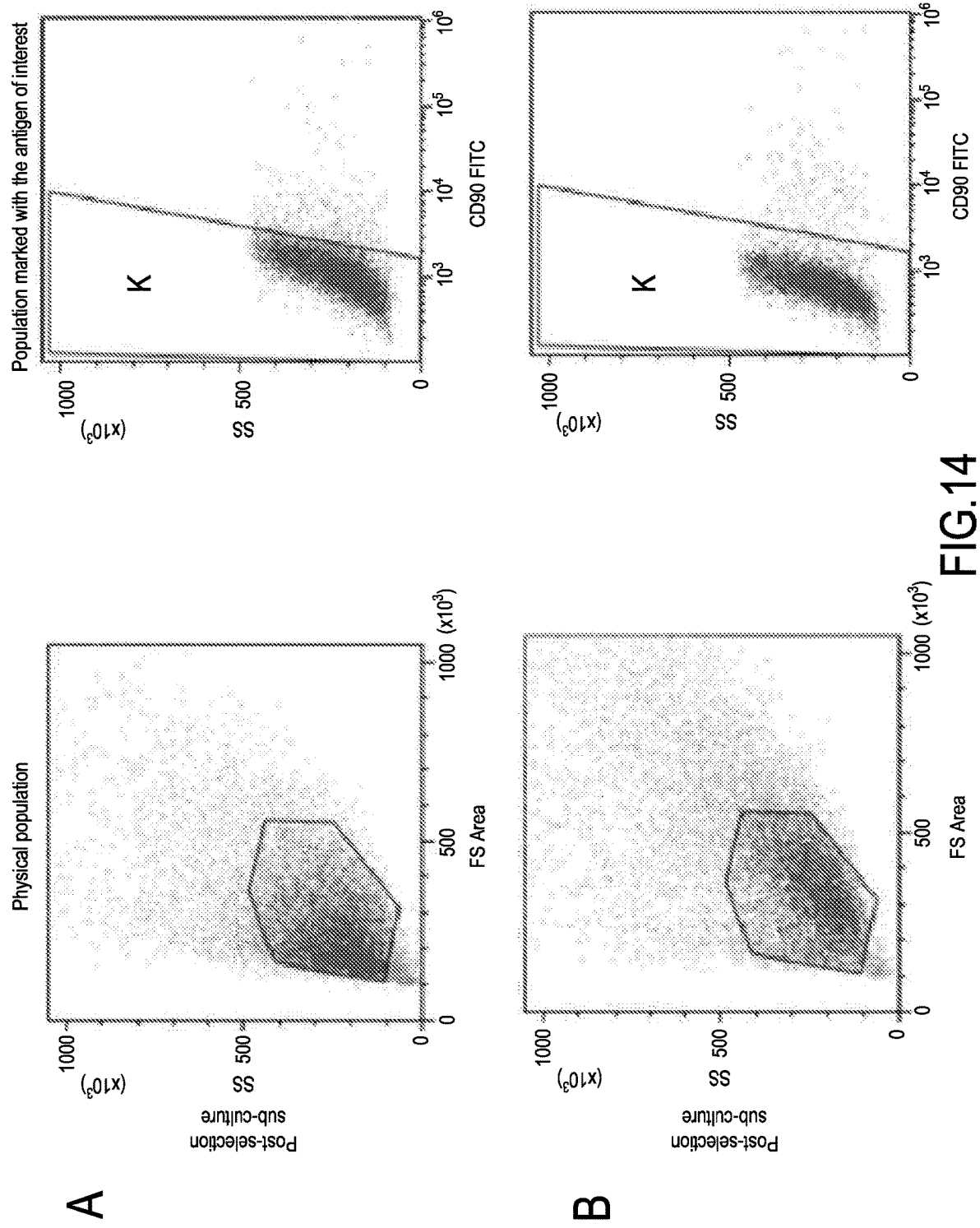

FIG. 14 shows graphs (immunosorting) that demonstrate the maintenance of the antigen of interest CD90 just selected (in this example negative selection visible inside gate I) and also after subculture of the selected cells.

Figure 15:
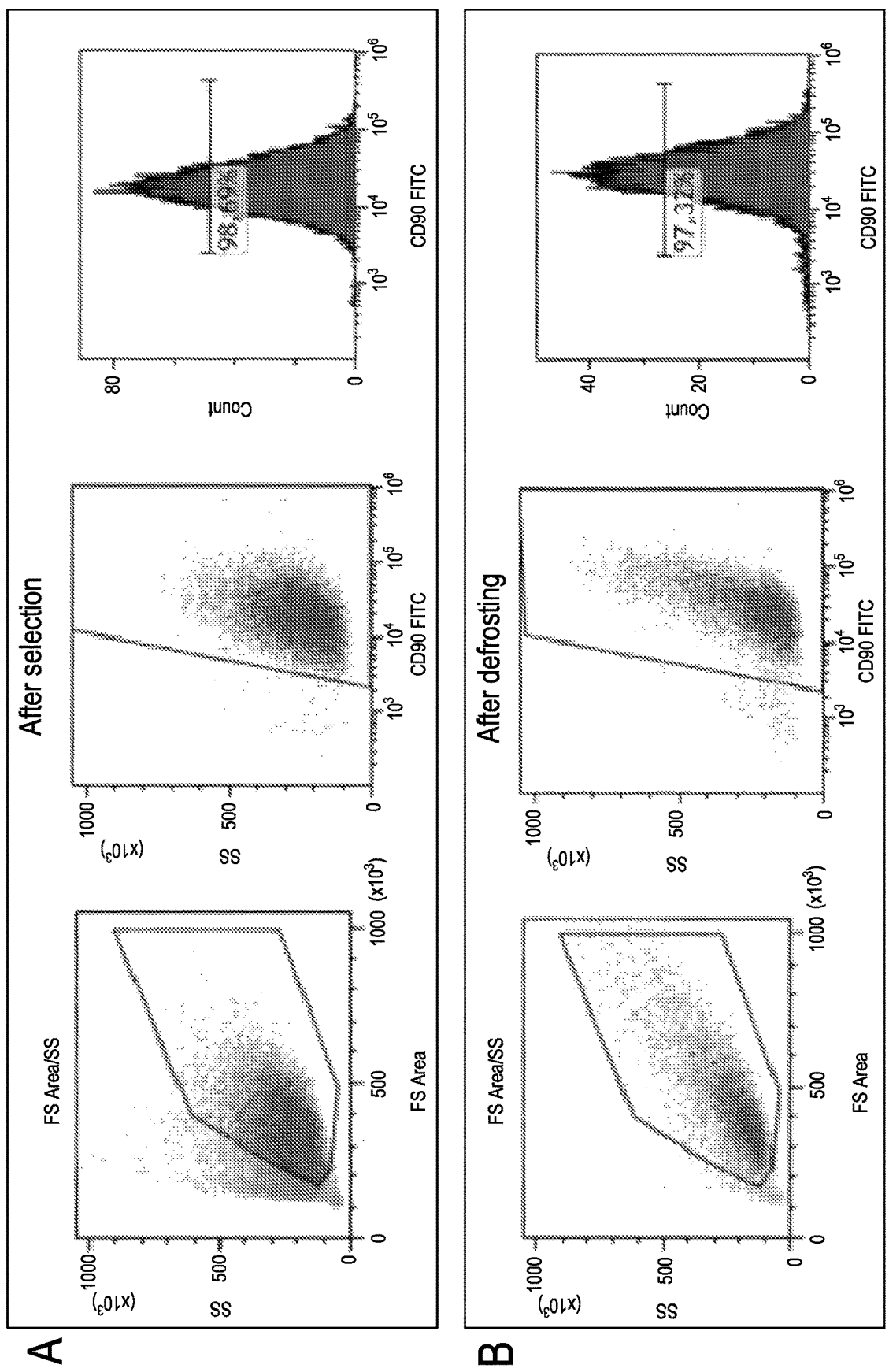

FIG. 15 shows an example of maintenance of the marker used for selection straight after selection and after freezing and defrosting. In the example, the positive selection was performed for the surface marker CD90 which is expressed by 98.67% of the population straight after isolation and 97.32% after the defrosting of the cells.

Figure 16:
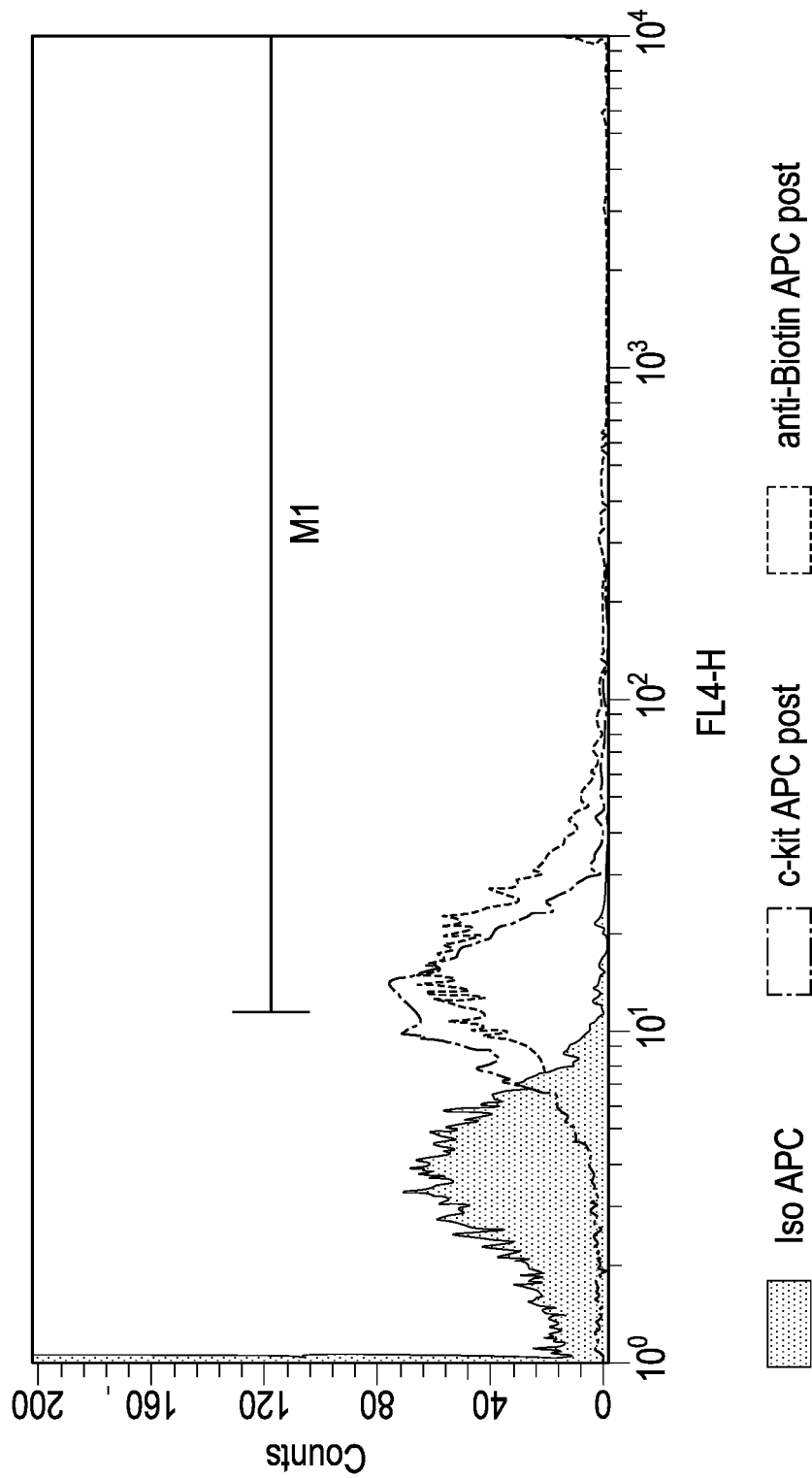

FIG. 16 is a diagram that shows a population of cardiac progenitors after selection characterized by positivity for c-kit in GMP conditions evaluated with both of the possible markings, using as negative control the isotype APC (full histogram), the APC human antibody anti-c-kit (grey broken line) and the antibody anti-biotin marked with APC (light continuous line).

FIG. 17 shows a table of the surface antigens evaluated in the sample of cardiac tissue of the auricle and septum.

Figure 18:
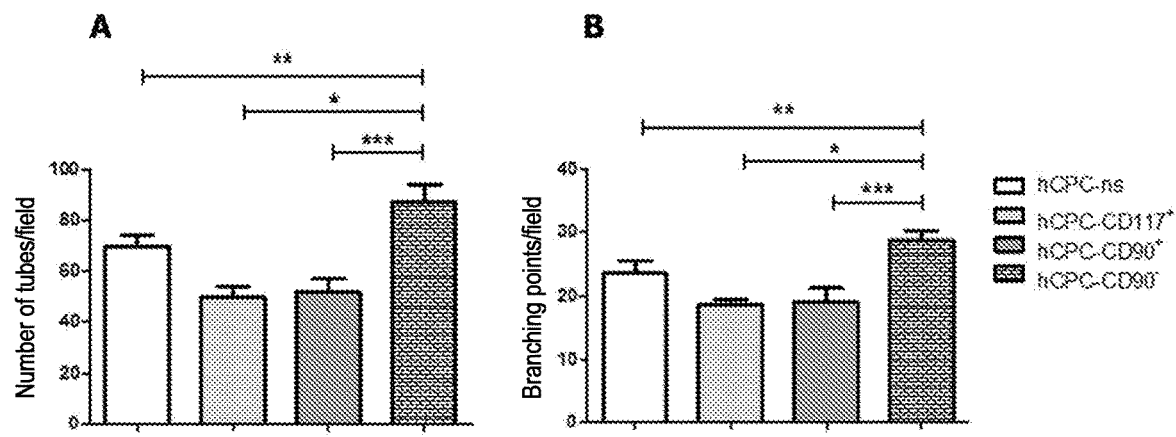

FIG. 18 shows endothelial differentiation of hCPC subpopulations assessed by Cultrex® assay. Results display tubular structures formation in hCPC-ns, hCPC-CD117$^+$, hCPC-CD90$^+$ and hCPC-CD90$^-$ on Cultrex® membrane. Panel A) Bar graphs show the quantification of tubular-like structures per microscopic field; Panel B) Bar graphs show the number of branching points between tubular-like structures. In these conditions hCPC-CD90$^-$ subpopulation produce a significant more tubular-like structures in 4 hours compared to the other subpopulations considered (hCPC-ns); (n=4) *p<0.05, p<0.05, *p<0.001.

Figure 19:
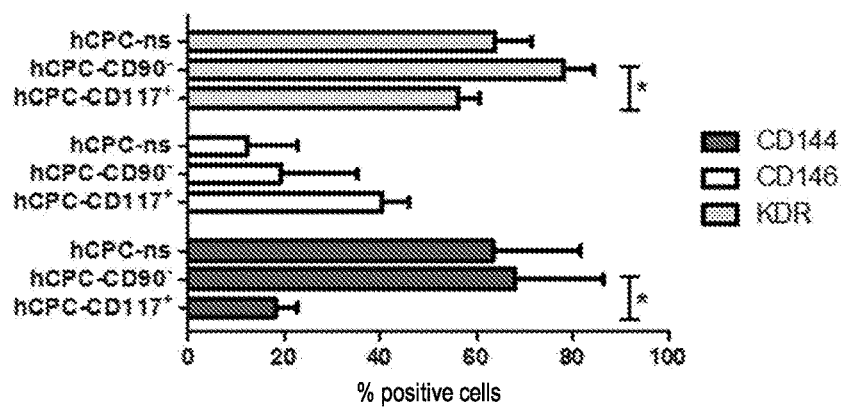

FIG. 19 shows endothelial differentiation of hCPC subpopulations evaluated by FACS analysis. Bar graph shows the comparison between VE-cadherin/CD144$^+$, CD146$^+$ and VEGFR-2/KDR$^+$ cells in hCPC-CD117$^+$ and hCPCCD90$^-$ cells after culturing into pro-angiogenic EGM-2 medium. In these conditions hCPC-CD90– cells shown a significant higher expression of endothelial markers CD144 and KDR. (n=4) *p<0.05.

Figure 20:
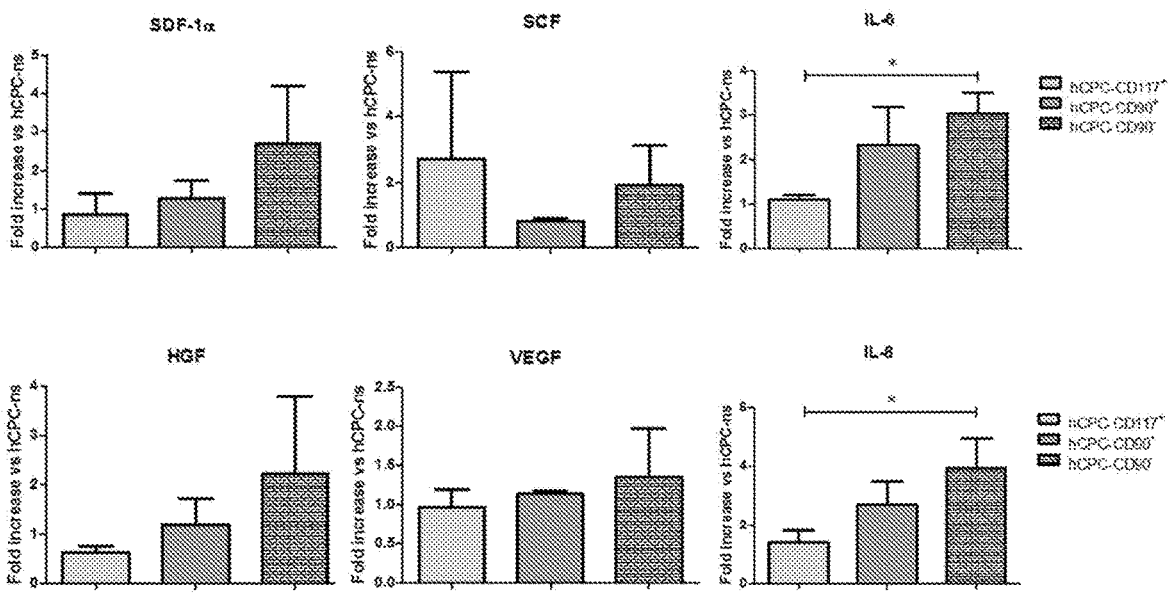

FIG. 20 shows the expression profiles of growth factors and cytokines in hCPC subpopulations. Bar graphs show an increase in cytokines and growth factors release in different hCPC subpopulations (hCPC-CD117$^+$, hCPC-CD90$^-$ and hCPC-CD90$^+$) compared to the unselected population (hCPC-ns). From the comparison hCPC-CD90$^-$ subpopulation shows an increased secretion profile for many factors, reaching the statistical significance for IL-6 and IL-8 compared to hCPC-CD117$^+$ subpopulation (n=3) *p<0.05.

Figure 21:
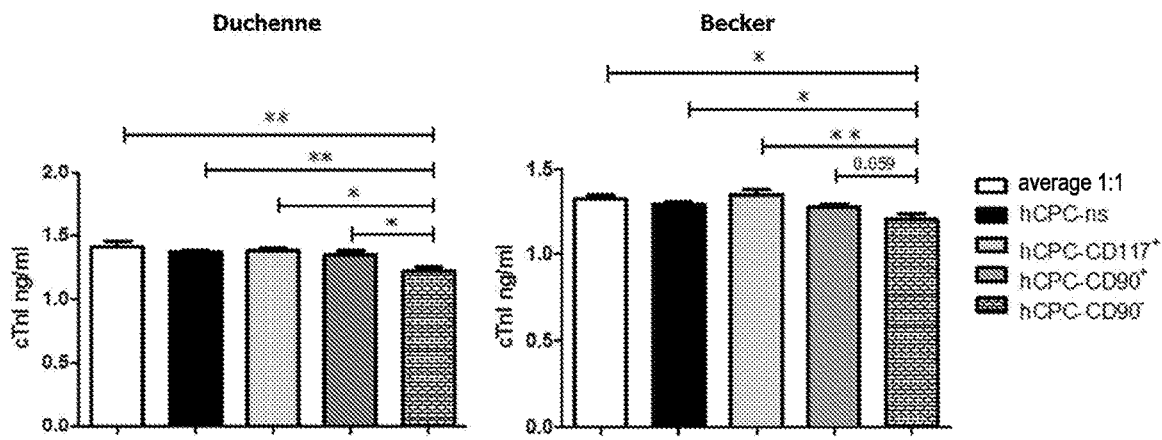

FIG. 21 shows cardioprotective potential of hCPC subpopulations. Bar graphs show the release of cardiac troponin isoform I (cTnI) in cardiomyocytes derived from iPS (CM-d-hiPSCs) from patients with dystrophic cardiomyopathy (Duchenne and Becker). It is evident that hCPC-CD90$^-$ subpopulation shows the highest and significant cardioprotective effect on both CM-d-hiPSCs populations, inducing the lowest troponin release. (n=6) *p<0.05, p<0.05, *p<0.001.

Figure 22:
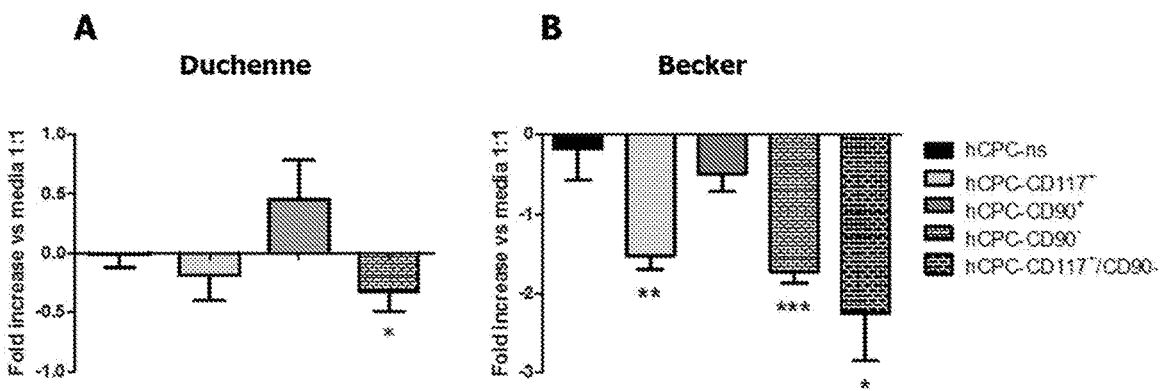

FIG. 22 shows the anti-inflammatory effect of hCPC subpopulations. Bar graphs show the release of TNF-α in cardiomyocytes derived from iPS (CM-d-hiPSCs) of patients with dystrophic cardiomyopathy. Panel A): TNF-α release in CM-d-hiPSCs supernatant (from Duchenne patients) co-cultured in the presence of hCPC-ns, hCPC-CD117$^+$, hCPC-CD90$^+$ and hCPC-CD90$^-$ after 3 days from the beginning of the co-culture; under these conditions the hCPC-CD90$^-$ subpopulation shows a significant anti-inflammatory effect, reducing the TNF-α release (n=4). Panel B: TNF-α release in CM-d-hiPSCs supernatant (from Becker patients) co-cultured with hCPC-ns, hCPC-CD117$^+$, hCPC-CD90$^+$ and hCPCCD90$^-$ 7 days after the beginning of the co-culture; under these conditions hCPC-CD90$^-$ and hCPC-CD117$^+$/CD90$^-$ subpopulations shows significant anti-inflammatory effect (n=6). *p<0.05, p<0.05, *p<0.001.

Figure 23:
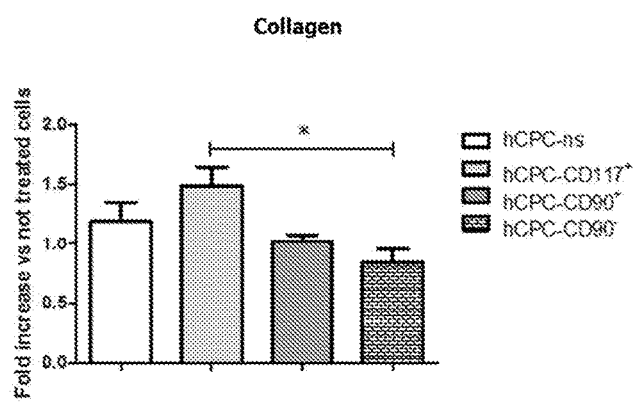

FIG. 23 shows myofibroblast differentiation of hCPC subpopulations evaluated by collagen production in vitro after TGF-β1 treatment for 5 days. The comparison shows that hCPC-CD90$^-$ subpopulation has the lowest ability to produce collagen compared to other populations considered (hCPC-ns, hCPC-CD117$^+$ and hCPC-CD90$^+$); (n=3)*p<0.

EXAMPLE 1

Figure 1:
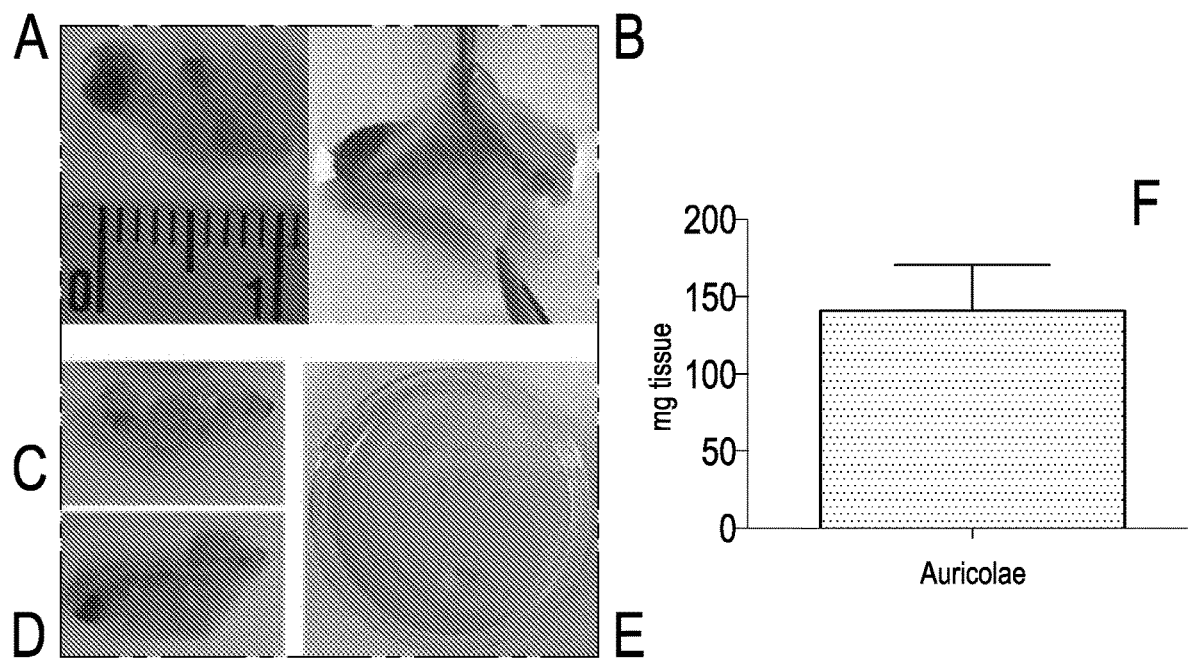

Method for the Isolation of a Population of Human Cardiac Progenitor Cells by Positive Selection Materials and Methods
Primary Culture The sample of human auricle with a weight comprised between 36.8 and 631.8 mg (see FIG. 1) is harvested in the operating theatre and immediately transferred into a sterile container containing at least one sterile solution to prevent the dehydration thereof (phosphate-buffered saline, PBS or physiological solution) and preferably a solution that also maintains the viability of the tissue (e.g. any culture medium)

Figure 2:
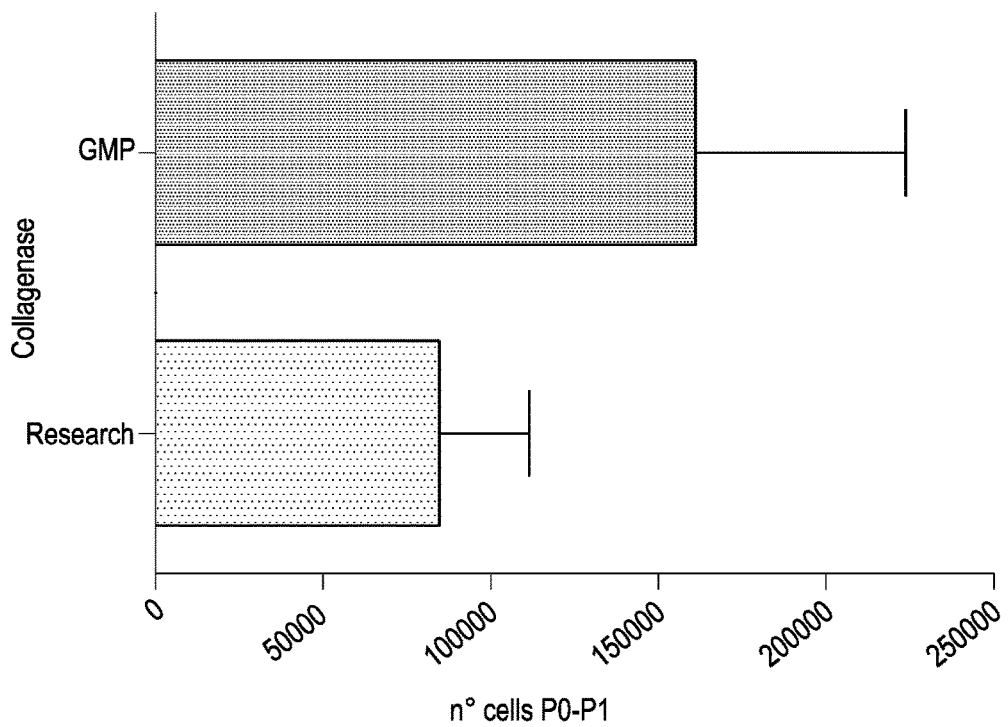
FIG. 2 shows two histograms of digestion of the cardiac tissue through the use of enzymatic solution according to research or GMP standards. The use of research and GMP enzymatic solution allows an equivalent number of cells to be obtained at the end of step 0 (P0-P1).
Figure 3:
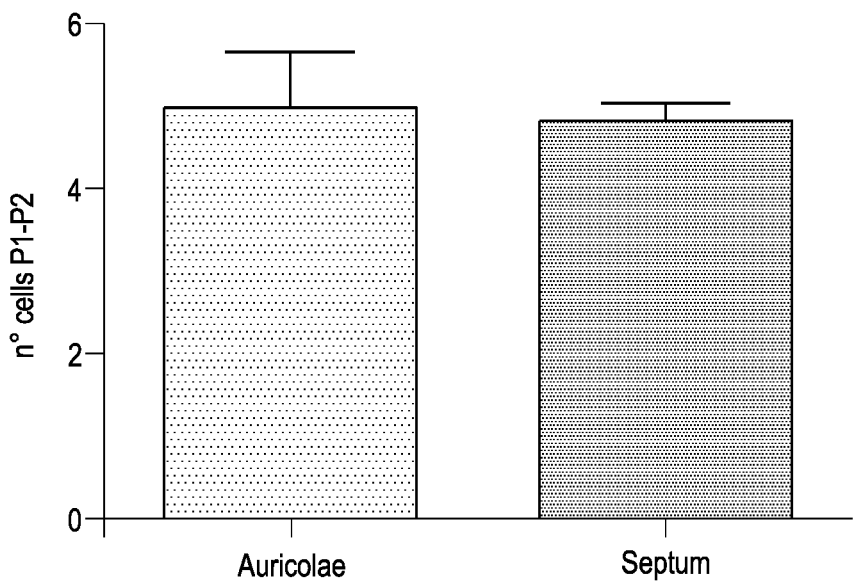
FIG. 3 shows two diagrams that reflect the examples of isolation of the cell population containing the cardiac progenitors from different sources of cardiac tissue (auricle and septum). From different regions of the heart a comparable number of cells can be obtained at the end of the first step (P1-P2) in the same conditions.

Alternatively, it is also possible to use another solution containing bovine serum albumin (BSA) or human serum albumin (HSA) or fetal bovine serum (FBS). From that moment the sample can be kept at controlled temperature (+4° C.) and processed within 48 hours or frozen in liquid nitrogen in a solution containing at least FBS and DMSO as the freezing does not have any effect on whether a culture is obtained (see FIG. 6a-b). For processing, after appropriate preparation with particular reference to the epicardium removal process, the fragment is weighed and minced using microsurgical tweezers and scissors into fragments of about 1-2 mm$^3$ and transferred into a tube together with the digestion solution (generally 1.7 ml of solution for every 100 mg of starting tissue). The digestion solution comprises basal culture medium, preferably Ham's/F12 containing collagenase NB4 (SERVA) at the concentration of 3 mg/ml (see FIG. 2).

Digestion of the Fragment
1. The tube(s) containing the fragments of tissue is/are transferred into a rotating oscillator that allows the movement of the fragments inside the tube at the temperature of 37° C. until the solution becomes cloudy due to the effective digestion of the fragments themselves (generally 30-40 minutes or up to 4 hours).
2. The tube(s) is/are recovered and the fragments that have not yet been digested can be deposited on the bottom of the tube; the "digested" solution (containing the cells) is recovered and transferred into a tube which, after the addition of PBS, will be centrifuged to allow the cells to be deposited on the bottom (it is centrifuged at 4° C. at 400 g for 10 minutes or 800 g for 5 minutes).
3. The supernatant is removed, the cells are re-suspended in complete medium and the tube containing the cells in ice is transferred, pending subsequent digestions. In the specific case, the complete medium is comprised of: Ham's/F12 containing 10% of fetal bovine serum (FBS), 2 mM L-glutathione and $5 \times 10^{-3}$ U/ml of human erythropoietin, 10 ng/mL of basic fibroblast growth factor (bFGF or FGF2) and antibiotics (penicillin up to 1000 U/ml and streptomycin up to 1000 ug/ml): F12H.

In the meantime a new digestion solution is added to the tube containing the fragments of tissue not yet digested repeating the previous steps 1-3 for a total of four times.

The four digestions conserved in ice are collected and transferred into a syringe connected to a syringe filter, (preferably of 70 µm) to be filtered in a new tube. The 4 tubes with complete medium are washed and the washing liquid is also transferred into the same syringe for filtering.

In the specific case, Ham's/F12 medium is used containing 10% of fetal bovine serum (FBS), 2 mM L-glutathione and $5 \times 10^{-3}$ U/ml of human erythropoietin, 10 ng/mL of basic fibroblast growth factor (bFGF or FGF2) and antibiotics (penicillin up to 1000 U/ml and streptomycin up to 1000 ug/ml): F12H.

The filtered solution is plated in a sterile capsule such as a Petri dish (generally one 100 mm diameter plate for every 100 mg of starting medium) (Day 1).

To allow the total digestion of the fragments still in the tube(s) a new digestion solution is added, preferably at a concentration of up to 0.3 mg/ml.

The tube(s) containing the fragments of tissue is/are transferred into a rotary oscillator that allows the movement of the fragments inside the tubes at the temperature of 37° C. for a whole night (about 16 hours).

The digested solution is filtered using a nylon mesh filter, preferably of 70 µm, and the filtrate is collected. The same filter is washed with PBS and the filtered solution is centrifuged to allow the cells to settle on the bottom.

The supernatant is removed, the cells are re-suspended in complete medium F12H and plated in a sterile capsule such as a Petri dish (generally a 100 mm diameter plate for every 100 mg of starting medium). The tube can be washed with complete medium F12H and the washing liquid transferred into the same Petri dish, for recovering any cells still in the tube (Day 2).

Figure 4:
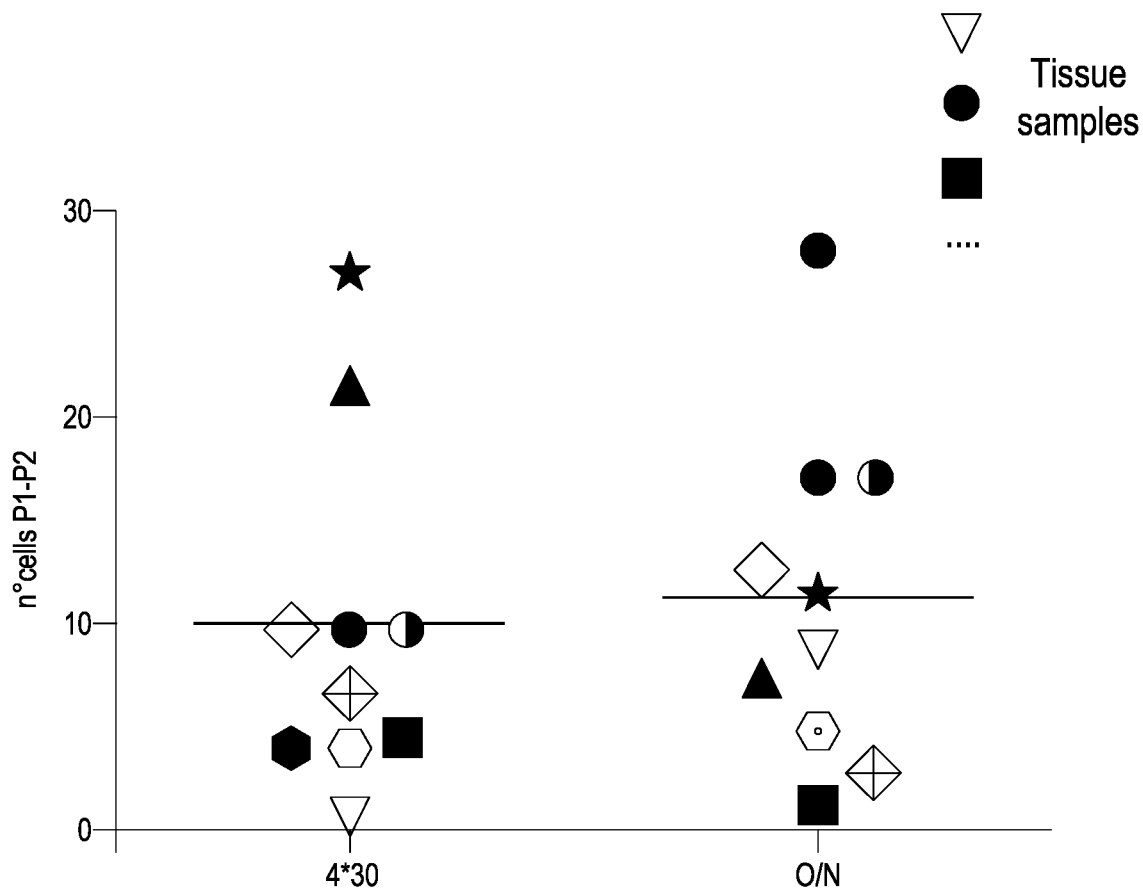
FIG. 4 shows a graph that demonstrates how the complete digestion of the fragment of cardiac tissue obtained by adding an O/N digestion of the tissue not yet digested after the first digestion step (4×30') doubles the number of cells that are obtained at the end of step 1 (P1-P2).

48 hours after being cultured (Day 3 for 4×30' digestions and Day 4 for the fragments digested all night) the culture medium containing the detritus, the dead cells or that have not adhered, are completely removed, the plate is washed with PBS and new fresh medium F12H is added (FIG. 4). The medium is changed, preferably every 2 days.

The growth of the cells is checked under the microscope and when about 70% confluence is reached or when the clones present become too confluent, the amplification of the cells is performed (FIG. 5).

Amplification of the Non-Selected Population
4. The culture medium is removed, the surface of the Petri capsule where the cells are plated is washed with PBS and the solution is added which can detach the cells from the plastic that is to be incubated at a controlled temperature of 37°C for the necessary time to obtain a cell suspension. For this process it is possible to use an enzyme solution (trypsin) or a non-enzyme solution (TrypLE™ Select, EDTA, Cell dissociation buffer or cell stripper).
5. The reaction is interrupted by the addition of a solution containing FBS (if the enzyme solution has been used) or PBS (if the non-enzyme solution has been used). The solution containing the cells is centrifuged in a tube.
6. The cells are counted and re-plated in F12H medium in a 1:10 dilution or preferably at the concentration of 1200-1500 cells/cm². The medium is changed, preferably every 2 days.

The growth of the cells is checked under the microscope and when 70% confluence is reached, further amplification of the cells is performed (by repeating steps 4 to 6). In fact, the further step does not compromise the frequency of the antigen of interest which identifies the population of interest that will be selected subsequently (FIG. 8). Alternatively, it is also possible to cryo-conserve the cell population obtained and complete the isolation at a later date as cryo-conservation does not compromise the frequency of the antigen of interest that identifies the population of interest that will be selected (see FIG. 6c).

Isolation of the Population of Interest by Positive Selection

The population to be isolated is detached from the Petri capsule using the non-enzymatic method (see section "Amplification of the non-selected population"), the cells are counted and re-suspended in the preferably cold isolation buffer (Wash Buffer, WB); in the specific case, PBS is used containing ethylenediaminetetraacetic acid (EDTA) and bovine serum albumin (BSA or HSA): the cells were re-suspended at the concentration of 100 µl every $1 \times 10^6$ cells.

A part of the cells (100,000 cells) are used for fluorescence-activated cell sorting (FACS) analysis before selection.

The cells were marked with IgG isotype immunoglobulin conjugated with the same fluorescent molecule bonded to the antibody that recognises the population of interest (in this example APC), and incubated for 15 minutes in the dark at ambient temperature or with the anti-biotin antibody marked with APC and incubated for 15 minutes in the dark at +4° C. After marking the cells were washed with WB and analysed with FACS (tube identified as isotype) (see FIG. 9a-b).

The remaining cells were marked with the antibody for selection; the cells were marked with anti-human CD117 antibody marked with biotin at the concentration of 2 µg every $1 \times 10^6$ cells for 20 minutes at +4° C. in agitation.

After marking the cells were washed with WB preferably cold and centrifuged. The supernatant was removed and the cells were re-suspended in WB at the concentration of 160 µL every $1 \times 10^6$ cells.

A part of the cells (100,000 cells) are used for fluorescence-activated cell sorting (FACS) analysis before selection. The cells were marked with anti-biotin antibody marked with APC, and incubated for 15 minutes in the dark at +4° C. After marking the cells were washed with WB and analysed through FACS (tube identified as Marked) (FIG. 9c).

The remaining cells are marked with the secondary antibody; microspheres were used with anti-biotin antibodies at the concentration of 40 µl every $1 \times 10^7$ cells, marking the cells for 15-20 minutes at +4° C. in agitation.

After marking the cells were washed with WB preferably cold and centrifuged. The supernatant was removed and the cells were re-suspended in cold WB; the cells were re-suspended in a volume of 500 µl up to $1.5 \times 10^6$ cells or 1 ml up to $15 \times 10^7$ cells for subsequent magnetic separation.

Magnetic Separation

The magnetic separation can be performed using, by way of example, the columns and the magnet made by the company Miltenyi. The column is activated using WB preferably cold (500 µl for the MS column and 1 ml for the LS column). The negative population is collected in a tube (NEG). The cells are transferred into the magnetic columns (up to $1.5 \times 10^6$ cells in an MS column or $15-30 \times 10^7$ cells in an LS column). The columns are washed 3 times adding WB preferably cold (500 µl for the MS column and 1 ml for the LS column). The positive population is recovered by squeezing the contents of the column into a tube after detaching it from the magnet and WB is added preferably cold (1 ml for the MS column and 2 ml for the LS column) (POS). To increase the selection purity, the positive cells selected (POS) can be passed into a new MS or LS magnetic column based on the expected number. To increase the number of positive cells selected it is possible to pass the cells of the NEG tube into a new MS or LS magnetic column based on the starting number. The positive (POS) and negative (NEG) cells were centrifuged, re-suspended in F12H medium and counted.

Also in this case a part of the cells (100,000 cells) is used for fluorescence-activated cell sorting (FACS) analysis (FIG. 9d) after selection in order to verify the purity thereof. The cells were marked with an anti-biotin antibody marked with APC, and incubated for 15 minutes in the dark at +4° C. (Miltenyi). After marking the cells were washed with WB and analysed through FACS.

After selection the cells can be frozen or plated in particular Transwell® plates equipped with culture inserts that allow the simultaneous culture of different types of cells that are physically separated but share the same culture medium (FIG. 13). In particular, the positive cells were plated in F12H medium on the bottom of the culture plate at a concentration comprised between 4,000-20,000 cells/cm$^2$ and the negative cells on the Transwell® insert at a concentration comprised between 3,000-10,000 cells/cm$^2$ or vice versa.

EXAMPLE 2

Method for the Isolation of a Population of Human Cardiac Progenitor Cells by Negative Selection The digestion steps of the fragment, primary culture and expansion before the selection are the same as in Example 1.

Isolation of the Population of Interest by Negative Selection

The population to be isolated is detached from the Petri dish using the non-enzymatic method (see section "Amplification of the non-selected population"), the cells are counted and re-suspended in the cold isolation buffer (WB); the cells were re-suspended at the concentration of 100 µl every $1\times10^7$ cells.

A part of the cells (100,000) is used for fluorescence-activated cell sorting (FACS) analysis before negative selection. The cells were marked with immunoglobulin (isotype IgG) conjugated with the same fluorescent molecule bonded to the antibody that recognizes the population of interest (in this example FITC, BD), 1 µl of antibody and incubated for 15 minutes in the dark at ambient temperature or with the anti-biotin FITC (Miltenyi) antibody, 10 µl of antibody and incubated for 15 minutes in the dark at +4° C.

After marking the cells were washed with WB and analysed through FACS (Isotype identified tube, see FIG. 10a-b).

The remaining cells were marked with the antibody for selection; the cells were marked with anti-human CD90 antibody conjugated with biotin (Miltenyi) at the concentration of 10 µl every $1\times10^7$ cells for 10 minutes at +4° C. or in ice.

After marking the cells were washed with cold WB and centrifuged. The supernatant was removed and the cells were re-suspended in WB at the concentration of 160 µl every $1\times10^6$ cells.

A part of the cells (100,000) is used for fluorescence-activated cell sorting (FACS) analysis before selection. The cells were marked with anti-biotin antibody marked with FITC (Miltenyi), 10 µl of antibody and incubated for 15 minutes in the dark at +4° C. After marking the cells were washed with WB and analysed through FACS (tube identified as Marked, FIG. 10c).

The remaining cells are marked with the secondary antibody; microspheres were used with anti-biotin antibodies (Miltenyi) at the concentration of 40 µl every $1\times10^7$ cells, marking the cells for 15-20 minutes at +4° C. in agitation.

After marking the cells were washed with cold WB and centrifuged. The supernatant was removed and the cells were re-suspended in cold WB; the cells were re-suspended at the concentration of 500 µl up to $30\times10^7$ cells for subsequent magnetic separation.

Magnetic Separation

The magnetic separation can be performed using the columns and the magnet made by the company Miltenyi. The column is activated using cold WB (2 ml for the LD column). The cells were transferred into the magnetic columns (up to $30\times10^7$ cells in an LD column). The columns were washed twice adding cold WB each time (1 ml for the LD column). The negative population is collected in a tube (NEG). To increase the selection purity, the negative cells selected (NEG) were passed into a new MS or LS magnetic column based on the expected number. In this case the negative population was recovered after passing the cells into a preactivated column (with cold WB) without any subsequent washing of the column itself. If the positive population is also to be collected, it is recovered by squeezing the contents of the column into a 15 ml tube after detaching it from the magnet and adding cold WB (POS). To increase the selection purity, the positive cells selected (POS) were passed into a new MS or LS magnetic column based on the expected number. The positive (POS) and negative (NEG) cells were centrifuged, re-suspended in F12H medium and counted.

A part of the cells (100,000 cells) is used for fluorescence-activated cell sorting (FACS) analysis after selection in order to verify the purity thereof. The cells were marked with anti-biotin antibody FITC (Miltenyi), 10 µl of antibody and incubated for 15 minutes in the dark at +4° C. After marking the cells were washed with WB and analysed through FACS (FIG. 10d).

After selection the cells can be frozen (see FIG. 15 for an example with positive selection) or plated at a concentration comprised between 3000-5000 cells/cm$^2$, considering the fact that their selected phenotype does not change (FIG. 14).

EXAMPLE 3

Method for the Isolation of a Population of Human Cardiac Progenitor Cells by Combined Positive and Negative Selection The digestion steps of the fragment, primary culture and expansion before the selection are the same as in Example 1.

Isolation of the Population of Interest by Combined Positive and Negative Selection The population to be isolated is detached from the Petri dish using the non-enzymatic method (see section "Amplification of the non-selected population"), the cells are counted and re-suspended in the cold isolation buffer (WB); the cells were not re-suspended at the concentration of 100 µl every $1\times10^7$ cells.

A part of the cells (400,000) is used for fluorescence-activated cell sorting (FACS) analysis before selection (FIG. 11A-E). Subsequently, the cells were divided into four different tubes.

The first tube (identified as Isotype FITC) was marked with the immunoglobulins (isotype IgG) conjugated with the same fluorescent molecule bonded to the antibody that recognizes the population of interest (in this example FITC, BD), 1 µl of antibody and incubated for 15 minutes in the dark at ambient temperature, the second tube (identified as Isotype APC, see FIG. 11C) was marked with the immunoglobulins conjugated with the same fluorescent molecule bonded to the antibody that recognises the population of interest (in this example APC, BD), the third and fourth tube (identified respectively as CD90 FITC and c-kit APC, see FIGS. 11D, E) were marked with the specific respective antibodies (CD90 FITC and c-kit APC, BD) up to 5 µl of antibody and incubated for 15 minutes in the dark at ambient temperature. After marking the cells were washed with WB and analysed through FACS.

The remaining cells were marked with the first antibody for selection (negative selection); the cells were marked with anti-human CD90 antibody conjugated to biotin (Miltenyi) at the concentration of 10 µL every $1\times10^7$ cells for 10 minutes at +4° C. or in ice.

After marking the cells were washed with cold WB and centrifuged. The supernatant was removed and the cells were re-suspended in WB at the concentration of 160 µl every $1\times10^6$ cells.

The cells are marked with the secondary antibody; microspheres were used with anti-biotin antibodies (Miltenyi) at the concentration of 40 µl every $1\times10^7$ cells, marking the cells for 15-20 minutes at +4° C. in agitation. After marking the cells were washed with cold WB and centrifuged. The supernatant was removed and the cells were re-suspended in cold WB; the cells were re-suspended at the concentration of 500 µl up to $30\times10^7$ cells for subsequent magnetic separation.

Negative Magnetic Separation

The magnetic separation can be performed using the columns and the magnet made by the company Miltenyi. The column is activated using cold WB (2 ml for the LD column). The cells are transferred into the magnetic columns (up to $30\times10^7$ cells in an LD column). The columns were washed twice adding cold WB each time (1 ml for the LD column). The negative population is collected in a tube (NEG). To increase the selection purity, the negative cells selected (NEG) were passed into a new MS or LS magnetic column based on the expected number. In this case the negative population was recovered after passing the cells into a pre-activated column (with cold WB) without any subsequent washing of the column itself. If the positive population is also to be collected, it is recovered by squeezing the contents of the column into a tube after detaching it from the magnet and adding cold WB (POS). To increase the selection purity, the positive cells selected (POS) can be passed into a new MS or LS magnetic column based on the expected number.

The negative cells (NEG) were centrifuged, re-suspended in cold WB and counted; the cells were not re-suspended at the concentration of 100 µl every $1\times10^6$ cells.

The cells were marked with the antibody for selection (positive selection); the cells were marked with anti-human CD117 antibody conjugated to biotin (Biolegend) at the concentration of 2 µg every $1\times10^6$ cells for 20 minutes at +4° C. in agitation.

After marking the cells were washed with cold WB and centrifuged. The supernatant was removed and the cells were re-suspended in WB at the concentration of 160 µl every $1\times10^6$ cells to be marked with the secondary antibody; microspheres were used with anti-biotin antibodies (Miltenyi) at the concentration of 40 µl every $1\times10^7$ cells, marking the cells for 15-20 minutes at +4° C. under agitation.

After marking the cells were washed with cold WB and centrifuged. The supernatant was removed and the cells were re-suspended in cold WB; the cells were re-suspended at the concentration of 500 µl up to $1.5\times10^6$ cells or at the concentration of 1 ml up to $15\times10^7$ cells for subsequent magnetic separation.

Positive Magnetic Separation

The magnetic separation can be performed using the columns and the magnet made by the company Miltenyi. The column is activated using cold WB (500 µl for the MS column and 1 ml for the LS column). The negative population is collected in a tube (NEG-NEG). The cells were transferred into the magnetic columns (up to $1.5\times10^6$ cells in an MS column or up to $30\times10^7$ cells in an LS column). The columns were washed 3 times adding cold WB each time (500 µl for the MS column and 1 ml for the LS column). The positive population was recovered by squeezing the contents of the column into a tube after detaching it from the magnet and adding cold WB (1 ml for the MS column and 2 ml for the LS column) (POS). To increase the selection purity, the positive cells selected (NEG-POS) were passed into a new MS or LS magnetic column based on the expected number. To increase the number of positive cells selected the cells of the NEG-NEG tube were passed into a new MS or LS magnetic column based on the starting number. The positive (NEG-POS) and negative (NEG-NEG) cells were centrifuged, re-suspended in F12H medium and counted.

A part of the cells (200,000 cells) was used for the fluorescence-activated cell sorting (FACS) analysis after selection in order to verify the purity thereof (see FIG. 11F). The cells were marked with mouse antibodies marked with APC anti-human CD117 (BD, up to 5 µl) and with antibodies marked with FITC anti-human CD90 (BD, 1 µl).

After selection the cells can be frozen or plated in particular Transwell® plates equipped with culture inserts that allow the simultaneous culture of different types of cells that are physically separated but share the same culture medium. In particular, the double selected cells (positivity for one marker and negativity for another) were plated in F12H medium on the bottom of the culture plate at a concentration comprised between 4000-20,000 cells/cm$^2$ and the cells of the same patient on the Transwell® insert at a concentration comprised between 3000-10,000 cells/cm$^2$ or vice versa (FIG. 13).

EXAMPLE 4

Implementation of the Method of Isolating Cardiac Progenitor Cells in GMP Conditions Materials and Methods Primary Culture The sample of human auricle (with a weight comprised between 36.8 and 631.8 mg) is collected in the operating theatre and immediately transferred into a sterile container containing a sterile solution to prevent the dehydration thereof (phosphate-buffered saline, PBS, physiological solution) and preferably a solution that also maintains the viability of the tissue (i.e. any culture medium).

Alternatively, it is also possible to use another solution containing bovine serum albumin (BSA) or fetal bovine serum (FBS).

From this moment the sample can be kept at controlled temperature (+4° C.) and preferably processed within 48 hours or frozen in liquid nitrogen in a solution suitable for the cryopreservative. For processing, the fragment is then minced mechanically. If the mincing envisages prior cleaning of the auricle of the epicardium that covers it, the fragment is cleaned before weighing, otherwise for protocols that do not require cleaning of the fragment, it is weighed with any epicardium still covering it.

For mechanical mincing, different equipment can be used that make the passage automatable. For example, the Medimachine (BD) and the GentleMACS (Miltenyi) machines were used.

Digestion of the Fragment

The minced tissues is then digested using collagenase NB-6 (GMP grade) adapting the method already developed for the basic study (FIG. 2):

1. The tube(s) containing the fragments of tissue is/are transferred into a rotating oscillator that allows the movement of the fragments inside the tube at the temperature of 37° C. until the solution becomes cloudy due to the effective digestion of the fragments themselves (generally 30-40 minutes or up to 4 hours).
2. The tube(s) is/are recovered and the fragments that have not yet been digested can be deposited on the bottom of the tube; the "digested" solution (containing the cells) is recovered and transferred into a tube which, after the addition of PBS, will be centrifuged at 4° C. to allow the cells to settle on the bottom.
3. The supernatant is removed and the cells are re-suspended in complete medium. In the specific case, Ham's/F12 medium is used containing 10% of GMP grade fetal bovine serum (FBS), 2 mM L-Glutathione and $5 \times 10^{-3}$ U/ml of human erythropoietin, 10 ng/mL of basic fibroblast growth factor (bFGF or FGF2) and antibiotics (penicillin up to 1000 U/ml and streptomycin up to 1000 ug/ml): F12G and the tube containing the cells in ice is transferred, pending subsequent digestions.

In the meantime a new digestion solution is added to the tube containing the fragments of tissue not yet digested repeating the previous steps 1 to 3 for a total of 4 times.

The digestions conserved in ice are collected and transferred into a syringe connected to a syringe filter, preferably of 70 μm to be filtered in a new tube. The tubes with complete medium F12G are washed and the washing liquid is also transferred into the same syringe for filtering.

The filtered solution is plated in a sterile capsule such as a Petri dish (generally one 100 mm diameter plate for every 100 mg of starting medium) (Day 1).

To allow the total digestion of the fragments still in the tube(s) a new digestion solution is added, preferably at a concentration of up to 0.3 mg/ml.

The tube(s) containing the fragments of tissue is/are transferred into a rotary oscillator that allows the movement of the fragments inside the tube at a temperature of about 37° C. for a whole night (about 16 hours).

The digested solution is filtered using a nylon mesh filter, preferably of 70 μm, and the filtrate is collected. The same filter is washed with PBS and the filtered solution is centrifuged to allow the cells to settle on the bottom.

The supernatant is removed, the cells are re-suspended in complete medium F12G and plated in a sterile capsule such as a Petri dish (generally a 100 mm diameter plate for every 100 mg of starting medium). The tube can be washed with complete medium F12G and the washing liquid transferred into the same Petri dish, for recovering any cells still in the tube (Day 2).

48 hours after being cultured (Day 3 for 4×30' digestions and Day 4 for the fragments digested all night) the culture medium containing the detritus, the dead cells or that have not adhered, are completely removed, the plate is washed with PBS and new fresh medium F12G is added (FIG. 4).

The medium is changed, preferably every 2 days.

The growth of the cells is checked under the microscope and when about 70% confluence is reached or when the clones present become too confluent, the amplification of the cells is performed (FIG. 5).

Amplification of the Non-Selected Population

4. The culture medium is removed and the surface of the Petri capsule where the cells are plated with PBS is washed and the non-enzymatic solution is added that is able to detach the cells from the plastic (TrypLE™ Select, Life Technologies). The non-enzymatic solution is incubated with the cells at controlled temperature, around 37° C. for the necessary time to obtain a cell suspension, from about 3 to 10 minutes.
5. The solution is inactivated by adding PBS. The solution containing the cells is centrifuged in a tube.
6. The cells are counted and re-plated in F12G medium in a 1:10 dilution or preferably at the concentration of 1200-1500 cells/cm$^2$. The medium is changed every two days.

The growth of the cells is counted under the microscope and when about 70% confluence is reached, further amplification of the cells is performed (see steps 4 to 6). For the extensive amplification, multi-flasks with 3 (525 cm$^2$) and 5 (875 cm$^2$) layers were used, such as cell-stacks with 5 layers (3180 cm$^2$).

Isolation of the Population of Interest by Positive Selection

The population to be isolated is detached from the multi-flask/cell-stack using the non-enzymatic method (see section "Amplification of the non-selected population"), the cells are counted and re-suspended in the isolation buffer (WB) preferably cold; in the specific case, PBS is used containing EDTA and HSA: the cells were re-suspended at the concentration of 100 μl every $1 \times 10^6$ cells.

A part of the cells (100,000) is used for fluorescence-activated cell sorting (FACS) analysis before selection. The cells were marked with immunoglobulin (IgG isotype) conjugated with the same fluorescent molecule bonded to the antibody that recognises the population of interest (in this example APC), and incubated for 15 minutes in the dark at ambient temperature or with the anti-biotin antibodies marked with APC (Miltenyi), incubated for 15 minutes in the dark at +4° C. After marking the cells were washed with WB and analysed with FACS (tube identified as Isotype).

The remaining cells were marked with the antibody for selection; the cells were marked with anti-human CD117 antibody marked with biotin (Biolegend) at the concentration of 2 μg every $1 \times 10^6$ cells for about 20 minutes at +4° C. in agitation.

After marking the cells were washed with cold WB and centrifuged. The supernatant was removed and the cells were re-suspended in WB at the concentration of 160 μl every $1 \times 10^6$ cells.

A part of the cells (100,000) are used for fluorescence-activated cell sorting (FACS) analysis before selection. The cells were marked with anti-biotin antibody marked with APC (Miltenyi), 10 μl of antibody and incubated for 15 minutes in the dark at +4° C. After marking the cells were washed with WB and analysed through FACS (tube identified as Marked).

The remaining cells are marked with the secondary antibody; microspheres were used with CliniMACS anti-biotin antibodies (Miltenyi) at the concentration of 40 µl every $1 \times 10^7$ cells, marking the cells for 15-20 minutes at about +4° C. in agitation.

After marking the cells were washed with cold WB and centrifuged. The supernatant was removed and the cells were re-suspended in cold WB; the cells were re-suspended in a volume of 1 ml every $1.6 \times 10^6$ cells for subsequent magnetic separation.

Magnetic Separation

The magnetic separation is performed using the instrument for magnetic selection intended for clinical use; CliniMACS Plus made by the company Miltenyi was used. Using a relevant program the positive cells were used, separated from the initial population and collected in a relevant bag, as for the negative cells.

A part of the cells (100,000) is used for fluorescence-activated cell sorting (FACS) analysis after selection in order to verify the purity thereof. The cells were marked with anti-biotin antibody marked with APC (Miltenyi), 10 µl of antibody and incubated for 15 minutes in the dark at +4° C. After marking the cells were washed with WB and analysed through FACS (FIG. 16).

After selection, the cells can be frozen without losing the marker expression (see FIG. 15, on CD90 positive) for which they were selected and then ready for clinical use for the cell therapy or transplantations.

EXAMPLE 5

Identification of the Surface Markers Selectable in Two Different Sources of Cardiac Cells Materials and Methods The digestion steps of the fragment, primary culture and expansion before selection are the same as in Example 1.

In this example three different samples of auricle and three different samples of septum were used.

At the end of the third passage the three auricle were counted, joined in a single sample and marked with the fluorescent marker VioBlue450 that makes all the cells in the V450 channel fluorescent. In the same way, the three samples from the septum were counted, joined in a single sample and marked with the fluorescent marker CFSE that makes all the cells in the FITC channel fluorescent.

The two cell populations were identified using the flow cytometer based on the marking used and subsequently the two cell populations were used to evaluate a panel of surface antigens.

The surface antigens evaluated in the sample of auricle and septum cardiac tissue are shown in the Table illustrated in FIG. 17.

The marking was performed following the instructions of the manufacturer of the commercial kit LEGENDScreen™ Lyophilized Antibody Panel Human Cell Screening (PE) Kit, BioLegend.

Using an appropriate gate strategy, the two cell populations were characterized for all the surface antigens illustrated in FIG. 17.

Table 2 represents the surface antigens expressed by the two different cell populations and the average expression of each antigen in the two cell sources. All the antigens expressed by at least one of the two sources used can be selected both with positive selection (see Example 1) and using negative selection (see Example 2) or, if appropriately combined also with a multiple selection of more than one marker (as shown for example in Example 3).

TABLE 2

| Antigen | Auricle % expression | Septum % expression |
| --- | --- | --- |
| CD1a | 1.5 | 0.97 |
| CD1b | 2.31 | 1.81 |
| CD1c | 1.02 | 0.72 |
| CD1d | 2.59 | 2.1 |
| CD2 | 0.8 | 0.72 |
| CD3 | 1.93 | 1.14 |
| CD4 | 0.82 | 0.72 |
| CD5 | 2.13 | 1.09 |
| CD6 | 0.94 | 0.53 |
| CD7 | 1.45 | 1.2 |
| CD8a | 0.09 | 0.21 |
| CD9 | 99.85 | 99.04 |
| CD10 | 17.99 | 14.45 |
| CD11a | 0.59 | 0.49 |
| CD11b | 2.84 | 1.81 |
| CD11b activated | 2.33 | 1.77 |
| CD11c | 1.23 | 0.79 |
| CD13 | 98.7 | 99.48 |
| CD14 | 5.79 | 6.16 |
| CD15 (SSEA-1) | 4.31 | 2.38 |
| CD16 | 1.1 | 0.94 |
| CD18 | 3.35 | 1.81 |
| CD19 | 1.1 | 0.98 |
| CD20 | 26.78 | 17.3 |
| CD21 | 0.48 | 0.58 |
| CD22 | 12.32 | 34.07 |
| CD23 | 1.17 | 0.76 |
| CD24 | 13.43 | 15.67 |
| CD25 | 1.67 | 2.25 |
| CD26 | 99.89 | 99.22 |
| CD27 | 1.88 | 1.59 |
| CD28 | 2.28 | 2.13 |
| CD29 | 99.89 | 83.08 |
| CD30 | 0.93 | 0.72 |
| CD31 | 7.05 | 9.01 |
| CD32 | 1.12 | 0.75 |
| CD33 | 3.81 | 2.74 |
| CD34 | 3.83 | 6.61 |
| CD35 | 1.64 | 1.14 |
| CD36 | 2.07 | 3.4 |
| CD38 | 2.35 | 1.97 |
| CD39 | 2.34 | 3.09 |
| CD40 | 1.56 | 3 |
| CD41 | 21.09 | 30.25 |
| CD42b | 1.06 | 0.88 |
| CD43 | 6.16 | 8.74 |
| CD44 | 99.86 | 90.38 |
| CD45 | 0.69 | 1.85 |
| CD45RA | 0.53 | 0.64 |
| CD45RB | 0.32 | 0.3 |
| CD45RO | 1.3 | 0.76 |
| CD46 | 85.69 | 87.43 |
| CD47 | 99.55 | 99.75 |
| CD48 | 2.65 | 1.69 |
| CD49a | 73.34 | 76.25 |
| CD49c | 99.93 | 99.8 |
| CD49d | 85.19 | 71.15 |
| CD49e | 99.92 | 99.92 |
| CD49f | 63.99 | 47.33 |
| CD50 (ICAM-3) | 0.35 | 0.22 |
| CD51 | 99.89 | 99.85 |
| CD51/61 | 93.35 | 94.24 |
| CD52 | 2.93 | 3.16 |
| CD53 | 0.37 | 0.57 |
| CD54 | 35.28 | 51.1 |
| CD55 | 85.71 | 90.12 |
| CD56 (NCAM) | 44.25 | 10.07 |
| CD57 | 46.31 | 10.95 |
| CD58 | 99.9 | 99.4 |
| CD59 | 99.61 | 28.22 |
| CD61 | 77.46 | 76.52 |

TABLE 2-continued

| Antigen | Auricle % expression | Septum % expression |
|---|---|---|
| CD62E | 1.59 | 1.21 |
| CD62L | 0.47 | 0.43 |
| CD62P (P-Selectin) | 1.05 | 0.99 |
| CD63 | 99.88 | 99.63 |
| CD64 | 4.13 | 2.79 |
| CD66a/c/e | 4.65 | 3.54 |
| CD66b | 1.54 | 1.51 |
| CD69 | 0.67 | 0.75 |
| CD70 | 3.63 | 2.28 |
| CD71 | 91.68 | 96.73 |
| CD73 | 99.86 | 99.54 |
| CD74 | 6.67 | 6.57 |
| CD79b | 2.84 | 2.27 |
| CD80 | 7.24 | 6.2 |
| CD81 | 99.95 | 98.85 |
| CD82 | 9.69 | 12.28 |
| CD83 | 5.79 | 4.86 |
| CD84 | 1.17 | 0.87 |
| CD85a (ILT5) | 0.79 | 0.83 |
| CD85d (ILT4) | 2.09 | 2.01 |
| CD85g (ILT7) | 0.6 | 0.54 |
| CD85h (ILT1) | 2.83 | 2.76 |
| CD85j (ILT2) | 6.9 | 10.53 |
| CD85k (ILT3) | 0.73 | 0.56 |
| CD86 | 3.01 | 1.71 |
| CD87 | 3.78 | 2.42 |
| CD88 | 4.13 | 2.72 |
| CD89 | 3.37 | 2.4 |
| CD90 (Thy1) | 57.31 | 31.11 |
| CD93 | 2.18 | 1.74 |
| CD94 | 1.32 | 0.68 |
| CD95 | 99.88 | 99.88 |
| CD96 | 1.11 | 0.93 |
| CD97 | 86.53 | 85.05 |
| CD99 | 99.96 | 98.81 |
| CD100 | 3.86 | 2.51 |
| CD101 (BB27) | 1.39 | 1.24 |
| CD102 | 5.62 | 7.61 |
| CD103 | 0.14 | 0.28 |
| CD104 | 1.92 | 1.35 |
| CD105 | 99.67 | 99.79 |
| CD106 | 2.47 | 2.52 |
| CD107a (LAMP-1) | 45.37 | 78.48 |
| CD108 | 71.97 | 71.34 |
| CD109 | 9.84 | 11.25 |
| CD111 | 12.42 | 3.75 |
| CD112 (Nectin-2) | 99.63 | 99.58 |
| CD114 | 4.22 | 2.84 |
| CD115 | 6.09 | 5.71 |
| CD116 | 3.17 | 2.68 |
| CD117 (c-kit) | 1.52 | 1.69 |
| CD119 (IFN-g R alpha chain) | 11.79 | 12.69 |
| CD122 | 0.38 | 0.27 |
| CD123 | 0.73 | 0.66 |
| CD124 | 3.8 | 3.24 |
| CD126 (IL-6 R alpha) | 1.74 | 0.9 |
| CD127 (IL7 R alpha) | 2.98 | 2.02 |
| CD129 (IL-9 R) | 5.6 | 3.85 |
| CD131 | 2.25 | 1.25 |
| CD132 | 18.51 | 18.69 |
| CD134 | 2.91 | 1.73 |
| CD135 | 3.57 | 2.25 |
| CD137 (4-1 BB) | 1.57 | 1.23 |
| CD137L (4-1 BB Ligand) | 7.54 | 5.28 |
| CD138 | 10.01 | 6.5 |
| CD140a | 22.98 | 30.17 |
| CD140b | 12.44 | 14.35 |
| CD141 | 18.82 | 12.35 |
| CD143 | 12.25 | 8.34 |
| CD143 | 4.87 | 3.22 |
| CD146 | 21.5 | 30.73 |
| CD148 | 28.73 | 27.96 |
| CD150 (SLAM) | 0.84 | 0.65 |
| CD152 | 1.92 | 1.38 |
| CD154 | 1.28 | 0.89 |
| CD155 (PVR) | 99.86 | 99.88 |
| CD156c (ADAM10) | 99.34 | 98.65 |
| CD158a/h | 3.61 | 1.81 |
| CD158b (KIR2DL2/L3, NKAT2) | 4.1 | 2.73 |
| CD158d | 4.62 | 3.07 |
| CD158e1 (KIR3DL1, NKB1) | 0.7 | 0.7 |
| CD158F | 3.05 | 1.71 |
| CD161 | 1.58 | 1.36 |
| CD162 | 1.8 | 1.62 |
| CD163 | 1.73 | 1.58 |
| CD164 | 72.23 | 89.2 |
| CD165 | 99.3 | 97.33 |
| CD166 | 99.98 | 98.95 |
| CD167a (DDR1) | 3.49 | 2.58 |
| CD169 | 0.6 | 0.46 |
| CD170 (Siglec-5) | 6.41 | 6.36 |
| CD172a (SIRPa) | 92.81 | 95.05 |
| CD172b (SIRPg) | 1.56 | 1.15 |
| CD172g (SIRPg) | 2.27 | 1.38 |
| CD178 (Fas-L) | 2.07 | 1.97 |
| CD179a | 4.52 | 3.09 |
| CD179b | 1.68 | 1.1 |
| CD180 (RP105) | 2.11 | 1.17 |
| CD181 (CXCR1) | 3.85 | 3.07 |
| CD182 (CXCR2) | 1.67 | 0.95 |
| CD183 | 5.1 | 3.37 |
| CD184 (CXCR4) | 7.1 | 5.72 |
| CD193 (CCR3) | 3.04 | 1.89 |
| CD195 (CCR5) | 5.37 | 3.17 |
| CD196 | 4.18 | 2.39 |
| CD197 (CCR7) | 4.64 | 2.83 |
| CD200 (OX2) | 99.91 | 98 |
| CD200 R | 3.07 | 1.91 |
| CD201 (EPCR) | 98.17 | 97.76 |
| CD202b (Tie2/Tek) | 3.45 | 2.97 |
| CD203c (E-NPP3) | 2.77 | 1.98 |
| CD205 (DEC-205) | 3.28 | 2.29 |
| CD206 (MMR) | 2.6 | 1.41 |
| CD207 (Langerin) | 1.68 | 1.15 |
| CD209 (DC-SIGN) | 2.3 | 1.1 |
| CD210 (IL-10 R) | 3.98 | 2.86 |
| CD213a2 | 4.65 | 1.38 |
| CD215 (IL-15 R alpha) | 3.6 | 1.93 |
| CD218a (IL-18R alpha) | 4.81 | 2.35 |
| CD220 | 32.22 | 29.95 |
| CD221 (IGF-1R) | 6.06 | 6.25 |
| CD226 (DNAM-1) | 3.47 | 1.61 |
| CD229 (Ly-9) | 0.69 | 0.57 |
| CD231 (TALLA) | 6.88 | 7.44 |
| CD235ab | 0.24 | 0.17 |
| CD243 | 68.87 | 48.28 |
| CD244 (2B4) | 15.24 | 5.51 |
| CD245 (p220/240) | 12.06 | 11.4 |
| CD252 (OX4OL) | 4.73 | 3.67 |
| CD253 (TRAIL) | 2.94 | 1.55 |
| CD254 | 16.21 | 12.96 |
| CD255 (TWEAK) | 18.07 | 11.67 |
| CD257 (BAFF, BLYS) | 56.98 | 55.05 |
| CD258 (LIGHT) | 15.21 | 15.97 |
| CD261 (DR4, TRAIL-R1) | 2.75 | 2.18 |
| CD262 (DR5, TRAIL-R2) | 89.8 | 89.17 |
| CD263 (DcR1, TRAIL-R3) | 9.14 | 7.25 |
| CD266 (Fn14, Receptor TWEAK) | 99.25 | 98.76 |
| CD267 (TACI) | 2.94 | 1.73 |
| CD268 (BAFF-R, BAFFR) | 1.56 | 1.18 |
| CD270 (HVEM) | 3.21 | 2.63 |
| CD271 | 1.99 | 1.37 |
| CD273 (B7-DC, PD-L2) | 88.65 | 90.05 |
| CD274 (B7-H1, PD-L1) | 95.91 | 98.3 |
| CD275 (B7-H2, B7-RP1, ICOSL) | 51.05 | 48.92 |
| CD276 | 99.73 | 99.56 |
| CD277 | 30.26 | 31.36 |
| CD278 (ICOS) | 0.96 | 0.64 |
| CD279 (PD-1) | 18.1 | 6.95 |
| CD282 (TLR2) | 75.58 | 62.64 |
| CD284 (TLR4) | 1.61 | 1.25 |
| CD286 (TLR6) | 1.93 | 1.28 |
| CD290 | 2.49 | 1.32 |
| CD294 | 3.53 | 2.53 |

TABLE 2-continued

| Antigen | Auricle % expression | Septum % expression |
|---|---|---|
| CD298 | 99.87 | 99.89 |
| CD300e (IREM-2) | 46.72 | 41.29 |
| CD300F | 2.33 | 1.43 |
| CD301 | 4.76 | 2.59 |
| CD303 | 0.96 | 0.62 |
| CD304 | 16.06 | 11.21 |
| CD307 | 1 | 1.19 |
| CD307d (FcRL4) | 3.51 | 2.55 |
| CD314 (NKG2D) | 7.4 | 5.3 |
| CD317 | 7.64 | 11.92 |
| CD318 (CDCP1) | 51.89 | 81.34 |
| CD319 (CRACC) | 4.84 | 4.6 |
| CD324 (E-Cadherin) | 3.18 | 1.87 |
| CD325 | 9.16 | 19.22 |
| CD326 (Ep-CAM) | 1.19 | 1.75 |
| CD328 (Siglec-7) | 1.1 | 0.68 |
| CD334 (FGFR4) | 1.36 | 1.73 |
| CD335 (NKp46) | 1.81 | 1.13 |
| CD336 (NKp44) | 1.12 | 0.98 |
| CD337 (NKp30) | 1.88 | 1.26 |
| CD338 (ABCG2) | 17.29 | 5.52 |
| CD340 (erbB2_HER-2) | 68.24 | 55.37 |
| CD344 (Frizzled-4) | 13.37 | 10 |
| CD351 | 2.56 | 2.44 |
| CD352 (NTB-A) | 3.05 | 2.01 |
| CD354 (TREM-1) | 2 | 1.74 |
| CD355 (CRTAM) | 2.09 | 1.63 |
| CD357 (GITR) | 4.67 | 2.63 |
| CD360 (IL-21R) | 5.63 | 4.17 |
| Microglobulin beta 2 | 99.98 | 99.62 |
| BTLA | 5.47 | 3.89 |
| C3AR | 33.01 | 18.95 |
| C5L2 | 7.23 | 4.24 |
| CCR10 | 5.15 | 3.48 |
| CLEC12A | 1.11 | 0.69 |
| CLEC9A | 3.46 | 2.35 |
| CX3CR1 | 8.88 | 7.3 |
| CXCR7 | 15 | 17.91 |
| delta-Opioid receptor | 2.17 | 1.74 |
| DLL1 | 3.77 | 3.71 |
| DLL4 | 0.39 | 0.33 |
| DR3 (TRAMP) | 3.47 | 1.73 |
| EGFR | 97.47 | 97.78 |
| erbB3/HER-3 | 1.24 | 0.83 |
| FceRl alpha | 3.26 | 1.38 |
| FcRL6 | 5.69 | 4.03 |
| Galectin-9 | 2.22 | 1.92 |
| GARP (LRRC32) | 7.01 | 21.48 |
| HLA-A, B, C | 99.49 | 98.85 |
| HLA-A2 | 40.58 | 98.35 |
| HLA-DQ | 0.52 | 0.34 |
| HLA-DR | 0.95 | 1.05 |
| HLA-E | 3.66 | 2.1 |
| HLA-G | 2.31 | 1.26 |
| IFN-g R b chain | 3.75 | 1.89 |
| Ig k light chain | 0.3 | 0.37 |
| Ig omega light chain | 0.37 | 0.38 |
| IgD | 2.11 | 2.17 |
| IgM | 0.7 | 0.54 |
| IL-28RA | 2.27 | 1.42 |
| Integrin alpha 9 beta1 | 3.25 | 1.77 |
| Integrin beta5 | 40.62 | 42.83 |
| Integrin beta7 | 3.1 | 2.03 |
| Jagged 2 | 4.91 | 3.49 |
| LAP | 1.43 | 1.21 |
| Lymphotoxin beta receptor (LT-bR) | 58.01 | 73.62 |
| Mac-2 (Galectin-3) | 4.63 | 2.73 |
| MAIR-II | 6.54 | 2.86 |
| MICA/MICB PE | 42.39 | 17.59 |
| MSC(W3D5) | 36.98 | 48.26 |
| MSC(W5C5) | 43.32 | 47.85 |
| MSC(W7C6) | 83.25 | 84.13 |
| MSC and NPC(W4A5) | 23.31 | 14.04 |
| MSCA-1(MSC, W8B2) | 27.37 | 24.37 |
| NKp80 | 2.01 | 1.53 |
| Notch1 | 2.02 | 1.84 |
| Notch2 | 5.61 | 4.48 |
| Notch3 | 2.63 | 2.56 |
| Notch4 | 4.44 | 3.63 |
| NPC(57D2) | 4.83 | 2.53 |
| Podoplanin | 17.38 | 11.96 |
| Pre-BCR | 9.62 | 16.57 |
| PSMA | 4.41 | 7.35 |
| Siglec-10 | 3.63 | 2.67 |
| Siglec-8 | 3.71 | 1.75 |
| Siglec-9 | 1.56 | 1.31 |
| SSEA-1 | 0.87 | 0.46 |
| SSEA-3 | 9.24 | 6.97 |
| SSEA-4 | 49.04 | 29.26 |
| SSEA-5 | 6.1 | 3.54 |
| TCRg/d | 8.72 | 4.67 |
| TCR Vbeta13.2 | 2.51 | 1.74 |
| TCR Vbeta23 | 6.27 | 7.81 |
| TCR Vbeta8 | 3.34 | 2.4 |
| TCR Vbeta9 | 1.36 | 0.86 |
| TCR Vdelta2 | 4.31 | 2.11 |
| TCR Vg9 | 4.52 | 2.95 |
| TCR V alpha 24-J alpha18 | 4.3 | 2.44 |
| TCR V alpha 7.2 | 3.41 | 2.06 |
| TCR alpha/beta | 5.51 | 3.38 |
| Tim-1 | 3.81 | 2.48 |
| Tim-3 | 2.09 | 1.8 |
| Tim-4 | 3.43 | 2.57 |
| TLT-2 | 4.08 | 2.57 |
| TRA-1-60R | 0.83 | 0.45 |
| TRA-1-81 | 1 | 0.57 |
| TSLPR (TSLP-R) | 3.02 | 2.11 |

EXAMPLE 6

Comparative Study with Respect to the Cardiac Cell Isolation Methods of the Prior Art A comparison was made between the number of cells, the purity and the cell viability, of the cell population obtained with the method according to the invention with respect to the prior art [4].

In the background the selection is performed using the Facs Cell Sorter (e.g., using the tool FacsAria BD) [4]. But, in this case it is only possible to select the population of cells that expresses at high levels the antigen used for selection (bright population), while it is not possible to obtain also the positive cells that express the antigen of interest but at low levels (positive Dim population).

With the method according to the present invention, it is possible to select all the cells that express the antigen of interest, regardless of the level of expression thereof.

FIG. 12 illustrates a diagram of the isolation method according to the invention that also allows the population to be selected that expresses the antigen of interest (c-kit) characterized by an intermediate or low mean fluorescence intensity (panel a). Panel b) shows a table comparing the number of cells, the purity and the cell viability, of the cell population obtained with the method according to the invention with respect to the prior art [4].

EXAMPLE 7

Phenotypic and Functional Characterization of Human Cardiac Progenitor Cell CD90− and CD117+/CD90− Subpopulations Obtained by the Method of the Invention Materials and Methods Patients and Tissue Samples Right human auricle samples were obtained from patients undergoing elective cardiac surgery procedures. The informed consent previously approved by the local ethic committee was obtained for each patient in accordance with the Declaration of Helsinki.

Flow Cytometry (FACS)

Immunophenotypic analysis of mesenchymal, haematopoietic and inflammatory markers was performed using multicolor flow cytometry on hCPC-CD90− cells. After detachment using a non-enzymatic solution, cells were resuspended in PBS containing 0.1% of BSA (Gibco, USA) and 2 mM EDTA (Gibco, USA) and incubated in the dark for 15 minutes with appropriate combinations of the following monoclonal antibodies or corresponding isotype: CD29-PE, CD44-PE, CD73-PE, CD105-APC, CD14 FITC, CD34-FITC, CD45-PE, HLA-DR-FITC, CD146-FITC (BD Pharmingen, Italy), CD200-FITC, KDR-PE (R & D Systems, USA) and CD144-Alexa700 (16B1 clone; eBioscience). The samples were then washed with 1 mL of wash buffer and centrifuged for 10 minutes at 400×g at 4° C. to remove unbound antibodies. The cells were resuspended in 250 µL of washing buffer and analyzed at the flow cytometer.

Endothelial Functional Assay and Differentiation

To evaluate the ability of hCPC-ns cells and the different subpopulations derived from them to form vascular structures in vitro, the cells were seeded on the basal membrane of Cultrex® (a soluble form of basement membrane purified from Engelbreth-Holm-Swarm (EHS) tumor from Trevigen, USA). Cultrex® was allowed to polymerize onto 48-well plates at 37° C., 5% $CO_2$ for 30 min. Cells were detached using a non-enzymatic solution, counted, diluted to $8 \times 10^4$ cells/ml in complete endothelial growth medium-2 (EGM-2, Lonza, Italy) and seeded to each well containing the Cultrex® matrix. The plates were incubated at 37° C., 5% $CO_2$ for 4 hours after which the number of capillary structures and the number of their branching points were counted. As a positive control in these experiments, HUVEC cells (Lonza, Italy) were used under the same culture conditions. Endothelial commitment was analyzed by culturing hCPC-ns and the different subpopulations derived from them (hCPC-CD117+, hCPC-CD90−) for 3 weeks in EGM-2 after which the immunophenotype was determined by flow cytometry.

Cytokine Secretion in the Culture Medium

To determine the expression of cytokines in the culture medium, the conditioned medium of hCPC-ns cells and the different subpopulations derived from them (hCPC-CD117+, hCPC-CD90+, hCPC-CD90−) was collected to measure the amount of soluble factors released in the culture medium within 48 hours. Subsequently, a microsphere-based multiplex immunoassay (Bio-Plex assay, Bio-Rad Laboratories) was used to compare the cytokines, chemokines and growth factors released in the culture medium. The culture medium was centrifuged at 4000 g for 10 minutes. The supernatant was collected and frozen at 80° C. until use. The samples were evaluated in duplicate due to the presence of the following angiogenic factors: the stromal cell-derived factor (SDF-1), the GRO (growth-regulated oncogene)-alpha (GRO-α), the stem cell factor (SCF), the leukemia inhibitory factor (LIF), interleukin-6 (IL-6), IL-8, IL-10, the monocyte chemoattractant protein 1 (MCP-1), the macrophages inflammatory protein 1 beta (MIP-1b), the Regulated on Activation Normal T Cell Expressed and Secreted (RANTES), vascular endothelial growth factor (VEGF) and hepatocyte growth factor (HGF), using the Luminex technology (Bio-Plex, Bio-Rad), according to the instructions for use.

Analysis of Cardiac Levels of Troponin-I (cTnI)

To determine the concentration of cTnI in the cardiomyocytes derived from iPs (CM-d-hiPSCs), a co-culture in Transwell® (pore 0.4 µm) was set up between CM-d-hiPSCs and hCPC-ns cells (and the different subpopulations derived from them, hCPC-CD117+, hCPC-CD90+, hCPC-CD90−). After 7 days from the beginning of the co-culture, the conditioned medium was collected and used for the cardiac troponin ELISA assay. The conditioned medium was centrifuged for 10 minutes at 4000 g and the supernatant used for the determination of cTnI concentration, using the chemiluminescent ELISA kit (Calbiotech) according to the instructions contained in the kit.

Analysis of TNF-α

To determine the TNF-α concentration in cardiomyocytes derived from iPs (CM-d-hiPSCs), a co-culture in Transwell® (pore 0.4 µm) was set up between CM-d-hiPSCs and hCPC-ns cells (and the different subpopulations derived from them, hCPC-CD117+, hCPC-CD90+, hCPC-CD90−). After 3 and 7 days from the beginning of the co-culture, the conditioned medium was collected and after centrifugation (10' to 4000 g) used for the ELISA (Invitrogen) assay, according to the instructions contained in the kit. To normalize the TNF content on the protein concentration of each sample on the same conditioned medium used for the ELISA assay, the protein dosage was also carried out using BCA (Pierce), measuring the absorbance at 540 nm.

Sircol™ Assay

The content of total soluble collagen in cell lysates and supernatant of hCPC-ns and the different subpopulations derived from them, hCPC-CD117+, hCPC-CD90+, hCPC-CD90−, treated with TGF-β1 for 5 days, was measured using Sircol™ assay (Biocolor) as described in the manufacturer's protocol. The amount of collagen was calculated according to a standard curve.

Statistical Analysis

Quantitative results are expressed as mean±standard deviation (SD) or standard error (SE). The variables were analyzed by the Student's t test. Statistical significance was evaluated with GraphPad Prism 5 and a value of $P<0.05$ was considered as statistically significant.

Results

Recently, it has emerged the idea that stem cells and/or progenitor cells used in cell therapy have a positive effect on the damaged myocardium through the production of soluble factors exerting a cardioprotective and anti-apoptotic action, increasing angiogenesis and modulating the inflammatory process. It is therefore crucial to find a cell population that is able to efficiently modulate these processes.

Immunophenotypic Characterization of hCPC-CD90− Cells

In agreement with that previously reported [4], the subpopulation of hCPC-CD90− cells equally maintains the phenotypic characteristics of mesenchymal cells, expressing typical mesenchymal markers (for example CD29, CD44, CD73 and CD200), and not expressing hematopoietic (eg CD14 and CD34) and immune system markers (HLA-DR).

Table 3 shows the characterization of hCPC-CD90⁻ at flow cytometry and indicates the expression of mesenchymal (CD29, CD44, CD73, CD105 and CD200), immune system (HLA-DR) and hematopoietic markers (CD34, CD45 and CD14). Data are expressed as mean±SE (n=9).

TABLE 3

| MARKER | CPC CD90⁻ Cells |
| --- | --- |
| CD29 | 97.20 ± 3.19 |
| CD44 | 97.46 ± 0.37 |
| CD73 | 95.75 ± 3.68 |
| CD105 | 96.92 ± 0.59 |
| CD200 | 90.18 ± 15.15 |
| HLA-DR | 0 ± 0 |
| CD34 | 1.76 ± 0.52 |
| CD45 | 0.64 ± 0.28 |
| CD14 | 90.18 ± 15.15 |

Endothelial Differentiation of hCPC-CD90⁻ Cells

The differentiation of hCPC-CD90⁻ cells was evaluated by functional assays and flow cytometry. After expansion, cells were tested for the ability to form tubular structures on the Cultrex® synthetic matrix, showing a significant increase in the number of new tubular structures ramifications after 4 h with respect to the other analyzed populations ((hCPC-CD117⁺, hCPC-CD90⁺, hCPC-CD90⁻) (FIG. 18).

Furthermore, hCPC-CD90⁻ cells were grown in proangiogenic medium EGM-2 for 3 weeks to establish their ability to differentiate into mature endothelial cells. Results showed that hCPC-CD90⁻ are more prone to differentiate into endothelial cells as indicated by the increased expression of endothelial markers CD144/Ve-cadherin and KDR/VEGFR2 compared to other considered populations of hCPC (hCPC-ns and hCPC-CD117⁺), reaching statistical significance when compared to hCPC-CD117⁺ cells (FIG. 19).

Analysis of Cytokine, Chemokine and Growth Factor Secretion by hCPC-CD90⁻ Cells

The pro-angiogenic potential of different hCPC subpopulations was tested through the use of multiplex analysis by comparing the cytokine content in the supernatant of hCPC-ns, hCPC-CD117⁺, hCPC-CD90⁺ and hCPC-CD90⁻. As shown in Table 4, a number of angiogenic cytokines were found in the supernatant of hCPC and sub-populations derived from them: SDF-1, Gro-α, SCF, LIF, IL-6, IL-8, IL-10, MCP-1, MIP-1b, RANTES, HGF and VEGF.

TABLE 4

| Cytokines | hCPC-ns | hCPC-CD90⁺ | hCPC-CD90⁻ |
| --- | --- | --- | --- |
| Sdf-1α | 20.20 ± 4.03 | 25.87 ± 9.45 | 54.38 ± 30.54 |
| Gro-α | 142 ± 35.71 | 380.3 ± 108.9 | 425.4 ± 82.91* |
| SCF | 0.03 ± 0.01 | 0.024 ± 0.002 | 0.078 ± 0.05 |
| LIF | 0.617 ± 0.44 | 0.65 ± 0.12 | 0.613 ± 0.23 |
| IL-6 | 555.8 ± 158.7 | 1289 ± 471.5 | 1679 ± 276.7* |
| IL-8 | 97.38 ± 23.21 | 261.8 ± 76.93 | 383.4 ± 96.02 |
| IL-10 | 0.007 ± 0.005 | 0.011 ± 0.009 | 0.129 ± 0.013 |
| MCP-1 | 188.1 ± 2.35 | 432.5 ± 124.8 | 685.2 ± 149.2** |
| MIP-1b | 0.085 ± 0.046 | 0.267 ± 0.109 | 0.326 ± 0.038* |
| RANTES | 0.083 ± 0.083 | 0.06 ± 0.06 | 0.094 ± 0.11 |
| VEGF | 30.71 ± 14.07 | 34.89 ± 1.34 | 41.35 ± 19.22 |
| HGF | 566 ± 324.5 | 676.5 ± 29.7 | 1257 ± 886.2 |

The Table indicates the expression of each cytokine in pg/ml/$10^5$ released by the cells in 48 hours and the results of the statistical comparison of factors produced by the 3 cell types with Student t-test. *=comparison respect to hCPC-ns; p<0.05 with t-test. Data are expressed as mean±SE (n=3).

In particular, we found that the levels of pro-angiogenic (Gro-α and IL-8) and pro-inflammatory cytokines (IL-6, MCP-1 and MIP-1b) were significantly enriched in the supernatant of hCPC-CD90⁻ compared to the unselected population (hCPC-ns) of the same patients, suggesting that the selected population shows a greater ability to produce factors compared to the unselected population of the same sample. Moreover, we analyze the secretion factor enrichment in hCPC-CD117⁺, hCPC-CD90⁺ and hCPC-CD90⁻ subpopulations, vs the unselected counterpart from the same patients (FIG. 20). The result shows an overexpression of almost all factors considered in the hCPC-CD90⁻ with respect to the hCPC-CD117⁺ subpopulation reaching the statistical significant for IL-6 and IL-8.

hCPC-CD90⁻ Mediates the Reversion of the Main Pathophysiological Characteristics of Duchenne and Becker's Muscular Dystrophy iPS-derived cardiomyocytes of dystrophic patients (DMD) (Duchenne and Becker dystrophy) exhibit a series of phenotypic deficits, typical of muscular dystrophy, including an increase in cardiomyocyte death and pro-inflammatory cytokine release such as tumor necrosis factor (TNF)-α, as described for other myocardial diseases [6]. The discovery of a cell population that antagonize multiple DMD pathophysiological pathways is crucial in the perspective of a possible exploitation in cell therapy. For this reason, several populations of hCPC were cultured in the presence of iPS-derived cardiomyocytes of dystrophic patients. Supernatant was collected after 3 and 7 days from the beginning of the co-culture and used to evaluate indices of cardiac damage occurring in the dystrophic disorder: the release of cardiac troponin I and of TNF-α in culture medium.

Cardioprotective Effect of hCPC-CD90⁻ Subpopulation

To evaluate the cardioprotective effect of different hCPC populations, they were co-cultured in the presence of CM-d-hiPSCs from Duchenne and Becker patients. Results showed that the subpopulation of hCPC-CD90⁻ is the only one, among those analyzed, able to significantly decrease the death of CM-d-hiPSCs of Duchenne and Becker patients (measured by the release of cTnI in the culture) after 7 days of culture (FIG. 21).

Anti-inflammatory Effect of hCPC-CD90– and hCPC CD117⁺/CD90⁻ Subpopulations

To evaluate the anti-inflammatory effect of different hCPC populations, cells were co-cultured in the presence of CM-d-hiPSCs of Duchenne and Becker patients. Results showed that the hCPC-CD90⁻ subpopulation is the only, one among those analyzed, able to significantly mitigate the damage occurring in CM-d-hiPSCs of Duchenne patients after 3 days of culture, as demonstrated by the reduced release of TNF-α in culture medium. As for CM-d-hiPSCs of Becker patients, displaying a less damaged phenotype, they positively respond to different considered subpopulations (hCPC-CD117⁺, hCPC-CD90⁻ and hCPC-CD117⁺/CD90⁻), showing a significant decrease in TNF-α release in the culture medium. In these conditions, the cell population, that appear to induce the more significant effect, is the hCPC-CD117⁺/CD90⁻ subpopulation followed by hCPC CD90⁻ subpopulation (FIG. 22).

In Vitro Effect of hCPC Treatment with TGF-β1

In the frame of cell therapy using progenitor cell of mesenchymal origin, it is necessary to look at the capability of these cells to differentiate into myofibroblasts which produce collagen, because this unwanted phenomenon could compromise the recovery of damaged myocardium.

Indeed, although collagen deposition is an essential and, normally, a reversible part of wound healing, the physiological tissue repair can evolve into a progressively irreversible fibrotic response when the accumulation of fibrotic connective tissue occurs (such as collagen and fibronectin) leading to permanent scarring, heart failure and ultimately death, as in heart failure.

In this context, it is crucial to have cells that, even in a pro-fibrotic context (with the increase of TGF-β1 expression), do not participate in the deposition of collagen. For this reason, we analyzed the effect of TGF-β1 treatment (5 days) to induce in different populations of hCPC the production of soluble collagen in the culture medium.

Results of the collagen quantification in these cells and in the culture medium by Sircol assay showed that hCPC-CD90⁻ subpopulation has the lowest ability to produce collagen compared to the other considered populations (hCPC-ns, hCPC-CD117⁺ and hCPC-CD90⁺) (FIG. 23).

REFERENCES

[1] Bolli R, Chugh A R, D'Amario D, Loughran J H, Stoddard M F, Ikram S, Beache G M, Wagner S G, Leri A, Hosoda T, Sanada F, Elmore J B, Goichberg P, Cappetta D, Solankhi N K, Fahsah I, Rokosh D G, Slaughter M S, Kajstura J, Anversa P, Lancet. November 2011. 26; 378(9806):1847-57.
[2] Makkar R R, Smith R R, Cheng K, Malliaras K, Thomson L E, Berman D, Czer L S, Marbán L, Mendizabal A, Johnston P V, Russell S D, Schuleri K H, Lardo A C, Gerstenblith G, Marbán E. Lancet. Marzo 2012. 10; 379(9819):895-904.
[3] Williams A R, Hatzistergos K E, Addicott B, McCall F, Carvalho D, Suncion V, Morales A R, Da Silva J, Sussman M A, Heldman A W, Hare J M. Circulation. Gennaio 2013. 15; 127(2):213-23.
[4] Gambini E, Pompilio G, Biondi A, Alamanni F, Capogrossi M C, Agrifoglio M, Pesce M. Cardiovasc Res. Febbraio 2011. Vol. 89(2):362-73.
[5] Gambini E. Pompilio G, Alamanni F, Capogrossi M C, Agrifoglio M, Persico L., Gambini A, Pesce M. Translational Res. November 2012. Vol. 160 (5):363-373.
[6] Diwan A., Tran T, Misra A M D. Curr Mol Med 2003; 3:161-182.

The invention claimed is:

1. A method for the isolation of human cardiac progenitor cells subpopulations, comprising the following steps:
   a) mincing a heart tissue sample containing a population of cardiac cells;
   b) 4-times progressive digestion of the cardiac tissue with an enzymatic mixture comprising collagenase and excluding trypsin in a concentration of between 0.1 and 3 mg/ml until a cell suspension is achieved and filtration is achieved through filters of size comprised between 30 μm and 100 μm;
   c) further digestion of residual cardiac tissue obtained in step b) for 16 hours with an enzymatic mixture comprising collagenase and excluding trypsin in a concentration of between 0.1 and 3 mg/ml until a cell suspension is achieved and filtration through filters of size comprised between 30 μm and 100 μm;
   d) culturing the cell suspension obtained in step b) and c) in a culture medium suitable to propagate the cardiac cells;
   e) preliminary expansion of the cell suspension obtained in step d) in a culture medium suitable to expand the cardiac cells in the presence of an enzymatic or non-enzymatic solution;
   f) secondary expansion of the cardiac cells obtained in step e) in a culture medium suitable to further expand the cardiac cells in the presence of an enzymatic or non enzymatic non-enzymatic solution;
   g) isolating one or more subpopulations of cardiac cells by positive and/or negative selection by the use of monoclonal antibodies directed against one or more surface antigens expressed in the starting population of cardiac progenitor cells.

2. The method for the isolation of human cardiac progenitor cell subpopulations according to claim 1, wherein said heart tissue sample of step a) is selected from the group consisting of right auricle, left auricle, septum, apex or ventricular biopsy.

3. The method for the isolation of human cardiac progenitor cell subpopulations according to claim 1, wherein step a) is performed automatically.

4. The method for the isolation of human cardiac progenitor cell subpopulations according to claim 1, wherein said enzymatic mixture of step b) and c) comprises a basal medium and an enzymatic solution.

5. The method for the isolation of human cardiac progenitor cells subpopulations according to claim 4, wherein said enzymatic solution comprises a mixture of collagenases.

6. The method for the isolation of human cardiac progenitor cells subpopulations according to claim 5, wherein said collagenase mixture comprises one or more enzymes selected from the group consisting of collagenase I, collagenase II, collagenase IV, and collagenase A.

7. The method for the isolation of human cardiac progenitor cells subpopulations according to claim 4, wherein said basal medium is Ham's/F12.

8. The method for the isolation of human cardiac progenitor cells subpopulations according to claim 1, wherein said medium suitable for propagating or multiplying and expanding the cardiac cells of steps d), e) and f) is Ham's/F12 medium supplemented with 10% fetal bovine serum, 2 mM L-glutathione and $5 \times 10^{-3}$ U/ml human erythropoietin, 10 ng/ml of basic fibroblast growth factor and antibiotics.

9. The method for the isolation of human cardiac progenitor cells subpopulations according to claim 1, wherein the enzymatic or non-enzymatic solution of step e) and f) for cell expansion is selected from the group consisting of a cell dissociation agent, a mixture of trypsin and/or EDTA, and Cell dissociation buffer.

10. The method for the isolation of human cardiac progenitor cells subpopulations according to claim 1, wherein said monoclonal antibodies of step g) are marked with biotin or a fluorescent molecule.

11. The method for the isolation of human cardiac progenitor cells subpopulations according to claim 10, wherein the biotin or fluorescent molecule is selected from FITC and APC.

12. The method for the isolation of human cardiac progenitor cells subpopulations according to claim 1, wherein said antibodies of step g) are monoclonal antibodies against one or more antigens selected from the following Table 1:

TABLE 1

| CD1a | CD1b | CD1c | CD1d | CD2 |
|------|------|------|------|-----|
| CD3  | CD4  | CD5  | CD6  | CD7 |

TABLE 1-continued

| | | | | |
|---|---|---|---|---|
| CD8a | CD9 | CD10 | CD11a | CD11b |
| CD11b activated | CD11c | CD13 | CD14 | CD15 (SSEA-1) |
| CD16 | CD18 | CD19 | CD20 | CD21 |
| CD22 | CD23 | CD24 | CD25 | CD26 |
| CD27 | CD28 | CD29 | CD30 | CD31 |
| CD32 | CD33 | CD34 | CD35 | CD36 |
| CD38 | CD39 | CD40 | CD41 | CD42b |
| CD43 | CD44 | CD45 | CD45RA | CD45RB |
| CD45R0 | CD46 | CD47 | CD48 | CD49a |
| CD49c | CD49d | CD49e | CD49f | CD50 (ICAM-3) |
| CD51 | CD51/61 | CD52 | CD53 | CD54 |
| CD55 | CD56 (NCAM) | CD57 | CD58 | CD59 |
| CD61 | CD62E | CD62L | CD62P (P-Selectin) | CD63 |
| CD64 | CD66a/c/e | CD66b | CD69 | CD70 |
| CD71 | CD73 | CD74 | CD79b | CD80 |
| CD81 | CD82 | CD83 | CD84 | CD85a (ILT5) |
| CD85d (ILT4) | CD85g (ILT7) | CD85h (ILT1) | CD85j (ILT2) | CD85k (ILT3) |
| CD86 | CD87 | CD88 | CD89 | CD90 (Thy1) |
| CD93 | CD94 | CD95 | CD96 | CD97 |
| CD99 | CD100 | CD101 (BB27) | CD102 | CD103 |
| CD104 | CD105 | CD106 | CD107a (LAMP-1) | CD108 |
| CD109 | CD111 | CD112 (Nectin-2) | CD114 | CD115 |
| CD116 | CD117 (c-kit) | CD119 (IFN-g R alpha chain) | CD122 | CD123 |
| CD124 | CD126 (IL-6 R alpha) | CD127 (IL7 R alpha) | CD129 (IL-9 R) | CD131 |
| CD132 | CD134 | CD135 | CD137 (4-1 BB) | CD137L (4-1 BB Ligand) |
| CD138 | CD140a | CD140b | CD141 | CD143 |
| CD143 | CD146 | CD148 | CD150 (SLAM) | CD152 |
| CD154 | CD155 (PVR) | CD156c (ADAM10) | CD158a/h | CD158b (KIR2DL2/L3, NKAT2) |
| CD158d | CD158e1 (KIR3DL1, NKB1) | CD158F | CD161 | CD162 |
| CD163 | CD164 | CD165 | CD166 | CD167a (DDR1) |
| CD169 | CD170 (Siglec-5) | CD172a (SIRPa) | CD172b (SIRPg) | CD172g (SIRPg) |
| CD178 (Fas-L) | CD179a | CD179b | CD180 (RP105) | CD181 (CXCR1) |
| CD182 (CXCR2) | CD183 | CD184 (CXCR4) | CD193 (CCR3) | CD195 (CCR5) |
| CD196 | CD197 (CCR7) | CD200 (OX2) | CD200 R | CD201 (EPCR) |
| CD202b (Tie2/Tek) | CD203c (E-NPP3) | CD205 (DEC-205) | CD206 (MMR) | CD207 (Langerin) |
| CD209 (DC-SIGN) | CD210 (IL-10 R) | CD213a2 | CD215 (IL-15 Ralpha) | CD218a (IL-18R alpha) |
| CD220 | CD221 (IGF-1R) | CD226 (DNAM-1) | CD229 (Ly-9) | CD231 (TALLA) |
| CD235ab | CD243 | CD244 (264) | CD245 (p220/240) | CD252 (OX4OL) |
| CD253 (Trail) | CD254 | CD255 (TWEAK) | CD257 (BAFF, BLYS) | CD258 (LIGHT) |
| CD261 (DR4, TRAIL-R1) | CD262 (DR5, TRAIL-R2) | CD263 (DcR1,TRAIL-R3) | CD266 (Fn14, TWEAK F | CD267 (TACI) |
| CD268 (BAFF-R, BAFFR) | CD270 (HVEM) | CD271 | CD273 (B7-DC, PD-L2) | CD274 (B7-H1, PD-L1) |
| CD275 (B7-H2, B7-RP1, ICOSL) | CD276 | CD277 | CD278 (ICOS) | CD279 (PD-1) |
| CD282 (TLR2) | CD284 (TLR4) | CD286 (TLR6) | CD290 | CD294 |
| CD298 | CD300e (IREM-2) | CD300F | CD301 | CD303 |
| CD304 | CD307 | CD307d (FcRL4) | CD314 (NKG2D) | CD317 |
| CD318 (CDCP1) | CD319 (CRACC) | CD324 (E-Cadherin) | CD325 | CD326 (Ep-CAM) |
| CD328 (Siglec-7) | CD334 (FGFR4) | CD335 (NKp46) | CD336 (NKp44) | CD337 (NKp30) |
| CD338 (ABCG2) | CD340 (erbB2_HER-2) | CD344 (Frizzled-4) | CD351 | CD352 (NTB-A) |
| CD354 (TREM-1) | CD355 (CRTAM) | CD357 (GITR) | CD360 (IL-21R) | beta2-microglobulin |
| BTLA | C3AR | C5L2 | CCR10 | CLEC12A |
| CLEC9A | CX3CR1 | CXCR7 | delta-Opioid Receptor | DLL1 |
| DLL4 | DR3 (TRAMP) | EGFR | erbB3/HER-3 | FceRIalpha |
| FcRL6 | Galectin-9 | GARP (LRRC32) | HLA-A, B, C | HLA-A2 |
| HLA-DQ | HLA-DR | HLA-E | HLA-G | IFN-g R b chain |
| Ig light chain k | Ig light chain omega | IgD | IgM | IL-28RA |
| Integrin alpha9beta1 | Integrin beta5 | Integrin beta7 | Jagged 2 | LAP |
| Lymphotoxin beta receptor (L | Mac-2 (Galectin-3) | MAIR-II | MICA/MICB PE | MSC(W3D5) |
| MSC(W5C5) | MSC(W7C6) | MSC and NPC(W4A5) | MSCA-1(MSC, W8B2) | NKp80 |
| Notch1 | Notch2 | Notch3 | Notch4 | NPC(57D2) |
| Podoplanin | Pre-BCR | PSMA | Siglec-10 | Siglec-8 |
| Siglec-9 | SSEA-1 | SSEA-3 | SSEA-4 | SSEA-5 |
| TCRg/d | TCR Vbeta13.2 | TCR Vbeta23 | TCR Vbeta8 | TCR Vbeta9 |
| TCR Vdelta2 | TCR Vg9 | TCR Valpha24-Jalpha18 | TCR Valpha7.2 | TCR alpha/beta |
| Tim-1 | Tim-3 | Tim-4 | TLT-2 | TRA-1-60R |
| TRA-1-81 | TSLPR (TSLP-R) | | | |

13. The method for the isolation of human cardiac progenitor cells subpopulations according to claim 1, wherein the selection of step g) is carried out by immunomagnetic separation.

14. The method for the isolation of human cardiac progenitor cells subpopulations according to claim 1, wherein said monoclonal antibodies of step g) are anti-CD117 and/or anti-CD90.

15. A subpopulation of human cardiac progenitor cells from human auricle obtained by the method of isolation according to claim 1 exclusively by negative selection using anti-CD90 monoclonal antibodies, characterized by a surface marker profile comprising expression of mesenchymal markers CD29, CD44, CD73, CD105 and CD200 and by lack of expression of CD90, hematopoietic markers CD34, CD45, and CD14 and the immune system marker HLA-DR.

16. A method of treating cardiovascular disease comprising administering the subpopulation of human cardiac progenitor cells according to claim 15, alone or in combination with another subpopulation of human cardiac progenitor cells.

17. The method of treating cardiovascular disease according to claim 16, wherein said method further comprises transplanting cardiac cells and/or tissue.

* * * * *